United States Patent
Omenetto et al.

(10) Patent No.: US 9,142,787 B2
(45) Date of Patent: Sep. 22, 2015

(54) SILK TRANSISTOR DEVICES

(71) Applicant: Tufts University/Trustees of Tufts College, Medford, MA (US)

(72) Inventors: Fiorenzo Omenetto, Wakefield, MA (US); David L. Kaplan, Concord, MA (US); Jason Amsden, Durham, NC (US); Raffaella Capelli, Bologna (IT); Stefano Toffanin, Padova (IT); Valentina Benfenati, Bologna (IT); Michele Muccini, Bologna (IT); Roberto Zamboni, Bologna (IT)

(73) Assignee: TUFTS UNIVERSITY, Medford, MA (US)

( * ) Notice: Subject to any disclaimer, the term of this patent is extended or adjusted under 35 U.S.C. 154(b) by 0 days.

(21) Appl. No.: 13/651,379

(22) Filed: Oct. 12, 2012

(65) Prior Publication Data

US 2014/0093902 A1 Apr. 3, 2014

Related U.S. Application Data

(63) Continuation of application No. 13/393,505, filed as application No. PCT/US2010/047307 on Aug. 31, 2010, now abandoned.

(60) Provisional application No. 61/238,319, filed on Aug. 31, 2009.

(51) Int. Cl.
 *H01L 51/00* (2006.01)
 *B82Y 10/00* (2011.01)
 (Continued)

(52) U.S. Cl.
 CPC .............. *H01L 51/0093* (2013.01); *B82Y 5/00* (2013.01); *B82Y 10/00* (2013.01);
 (Continued)

(58) Field of Classification Search
 CPC ............ H01L 51/0545; H01L 51/0036; H01L 51/0541; H01L 51/0558
 USPC ................. 257/40, E51.007, E51.025, 51, 52
 See application file for complete search history.

(56) References Cited

U.S. PATENT DOCUMENTS

| | | | |
|---|---|---|---|
| 4,676,640 A | 6/1987 | Briggs | |
| 5,252,285 A | 10/1993 | Lock | |

(Continued)

FOREIGN PATENT DOCUMENTS

| | | |
|---|---|---|
| EP | 0245509 A1 | 11/1987 |
| EP | 1025988 A1 | 8/2000 |

(Continued)

OTHER PUBLICATIONS

Bai, J. et al., Regenerated spider silk as a new biomaterial for MEMS, Biomed Microdevices, 8:317-323 (2006).

(Continued)

*Primary Examiner* — Chuong A Luu
*Assistant Examiner* — Rodolfo Fortich
(74) *Attorney, Agent, or Firm* — Choate Hall & Stewart, LLP

(57) ABSTRACT

The invention relates to ecosustainable and biocompatible, low cost, ambient friendly electronic and optoelectronic devices, such as transistors and light-emitting transistors, made with silk fibroin or blended with other biopolymers, methods for fabrication and methods of using the silk-based electronics and optoelectronics. The silk-based electronics and optoelectronics can be implanted in vivo and in vitro for biomedical applications, such as for drug discovery or drug screening assays and devices. The silk-based devices may be used in the food industry and embedded in packaging for tracking and sensing, for security purposes or exploited as disposable not harmful for the environment efficient general electronic and optoelectronic devices.

11 Claims, 8 Drawing Sheets

(51) Int. Cl.
  *H01L 51/05*  (2006.01)
  *H01L 51/52*  (2006.01)
  *B82Y 5/00*  (2011.01)
  *C07K 14/435*  (2006.01)
  *G01N 33/50*  (2006.01)

(52) U.S. Cl.
  CPC ....... *C07K 14/43586* (2013.01); *G01N 33/502* (2013.01); *H01L 51/052* (2013.01); *H01L 51/0566* (2013.01); *H01L 51/5296* (2013.01); *H01L 51/0036* (2013.01); *H01L 51/0053* (2013.01); *H01L 51/0545* (2013.01); *H01L 51/0562* (2013.01)

(56) References Cited

U.S. PATENT DOCUMENTS

| | | |
|---|---|---|
| 5,427,096 A | 6/1995 | Bogusiewicz et al. |
| 5,512,218 A | 4/1996 | Gresser et al. |
| 6,134,045 A | 10/2000 | Jiang et al. |
| 6,150,491 A | 11/2000 | Akkara |
| 6,284,418 B1 | 9/2001 | Trantolo |
| 6,924,503 B2 | 8/2005 | Cheng et al. |
| 6,989,897 B2 | 1/2006 | Chan et al. |
| 6,992,325 B2 | 1/2006 | Huang |
| 7,223,609 B2 | 5/2007 | Anvar et al. |
| 7,713,778 B2 | 5/2010 | Li et al. |
| 8,005,526 B2 | 8/2011 | Martin et al. |
| 2001/0002417 A1 | 5/2001 | Akkara et al. |
| 2001/0003043 A1 | 6/2001 | Metspalu et al. |
| 2003/0203366 A1 | 10/2003 | Lim et al. |
| 2003/0214057 A1 | 11/2003 | Huang |
| 2004/0001299 A1 | 1/2004 | van Haaster et al. |
| 2004/0029241 A1 | 2/2004 | Hahn et al. |
| 2004/0081384 A1 | 4/2004 | Datesman et al. |
| 2004/0229349 A1 | 11/2004 | Daridon |
| 2005/0008675 A1 | 1/2005 | Bhatia et al. |
| 2005/0151966 A1 | 7/2005 | Packirisamy et al. |
| 2005/0194365 A1 | 9/2005 | Li |
| 2005/0213868 A1 | 9/2005 | Cunningham |
| 2005/0217990 A1 | 10/2005 | Sibbett et al. |
| 2005/0276791 A1 | 12/2005 | Hansford et al. |
| 2006/0042822 A1 | 3/2006 | Azeyanagi et al. |
| 2006/0079454 A1* | 4/2006 | Reches et al. ................ 514/12 |
| 2006/0091571 A1 | 5/2006 | Akutsu et al. |
| 2006/0134606 A1 | 6/2006 | Montagu |
| 2006/0141617 A1 | 6/2006 | Desai et al. |
| 2006/0177479 A1 | 8/2006 | Giachelli et al. |
| 2006/0178655 A1 | 8/2006 | Santini et al. |
| 2006/0226575 A1 | 10/2006 | Maghribi et al. |
| 2006/0236436 A1 | 10/2006 | Li et al. |
| 2007/0007661 A1 | 1/2007 | Burgess et al. |
| 2007/0009968 A1 | 1/2007 | Cunningham et al. |
| 2007/0026064 A1 | 2/2007 | Yoder et al. |
| 2007/0031607 A1 | 2/2007 | Dubson et al. |
| 2007/0042505 A1 | 2/2007 | Israel et al. |
| 2007/0058254 A1 | 3/2007 | Kim |
| 2007/0073130 A1 | 3/2007 | Finch et al. |
| 2007/0178240 A1 | 8/2007 | Yamazaki et al. |
| 2007/0233208 A1 | 10/2007 | Kurtz et al. |
| 2008/0019925 A1 | 1/2008 | Begleiter |
| 2008/0038236 A1 | 2/2008 | Gimble et al. |
| 2008/0152281 A1 | 6/2008 | Lundquist et al. |
| 2008/0203431 A1 | 8/2008 | Garcia et al. |
| 2008/0239755 A1 | 10/2008 | Parker et al. |
| 2008/0288037 A1 | 11/2008 | Neysmith et al. |
| 2009/0028910 A1 | 1/2009 | DeSimone et al. |
| 2009/0208555 A1 | 8/2009 | Kuttler et al. |
| 2010/0028451 A1 | 2/2010 | Kaplan et al. |
| 2010/0063404 A1 | 3/2010 | Kaplan et al. |
| 2010/0120116 A1 | 5/2010 | Kaplan et al. |

FOREIGN PATENT DOCUMENTS

| | | |
|---|---|---|
| EP | 1116987 A2 | 7/2001 |
| EP | 1166987 A2 | 1/2002 |
| EP | 1467224 A1 | 10/2004 |
| JP | 60142259 A | 7/1985 |
| JP | 60155129 A | 8/1985 |
| JP | 1989135853 | 5/1989 |
| JP | 01280242 A | 11/1989 |
| JP | 02086799 A | 3/1990 |
| JP | 11042106 A | 2/1999 |
| JP | 1999123791 | 5/1999 |
| JP | 1999183854 | 7/1999 |
| JP | 2000096490 A | 4/2000 |
| JP | 2000143472 A | 5/2000 |
| JP | 2000180969 A | 6/2000 |
| JP | 2001147301 A | 5/2001 |
| JP | 2001280242 A | 10/2001 |
| JP | 2002287377 A | 10/2002 |
| JP | 2003195001 A | 7/2003 |
| JP | 2003322729 A | 11/2003 |
| JP | 2004162209 A | 6/2004 |
| JP | 2004307661 A | 11/2004 |
| JP | 2005530983 A | 10/2005 |
| JP | 2006119424 A | 5/2006 |
| JP | 2006241450 A | 9/2006 |
| KR | 20060027113 A | 3/2006 |
| KR | 20070060822 A | 6/2007 |
| KR | 20080069553 A | 7/2008 |
| WO | WO-9315244 A1 | 8/1993 |
| WO | WO-0031752 A2 | 6/2000 |
| WO | WO-0110464 A1 | 2/2001 |
| WO | WO-0185637 A2 | 11/2001 |
| WO | WO-03038033 A2 | 5/2003 |
| WO | WO-2004000915 A2 | 12/2003 |
| WO | WO-2004092250 A1 | 10/2004 |
| WO | WO-2005012606 A2 | 2/2005 |
| WO | WO-2005019503 A2 | 3/2005 |
| WO | WO-2005031724 A1 | 4/2005 |
| WO | WO-2006020507 A1 | 2/2006 |
| WO | WO-2006/027780 A2 | 3/2006 |
| WO | WO-2008085904 A1 | 7/2008 |
| WO | WO 2008085904 A1 * | 7/2008 |
| WO | WO-2008/127401 A2 | 10/2008 |
| WO | WO-2008118211 A2 | 10/2008 |
| WO | WO-2008127403 A2 | 10/2008 |
| WO | WO-2008127405 A2 | 10/2008 |
| WO | WO-2009061823 A1 | 5/2009 |
| WO | WO-2010/022353 A1 | 2/2010 |
| WO | WO-2010042798 A2 | 4/2010 |
| WO | WO-2010059963 A2 | 5/2010 |

OTHER PUBLICATIONS

Chrisey, D.B. et al., Laser Deposition of Polymer and Biomaterial Films, Chem. Rev 103(2):553-576 (2003).
Extended European Search Report of EP09767706.6, 6 pages (Jan. 8, 2013).
Extended European Search Report of EP10812751.5, 10 pages (Feb. 8, 2013).
Fukuoka T. et al., Enzymatic Polymerization of Tyrosine Derivatives. Peroxidase- and Protease-Catalyzed Synthesis of Poly(tyrosine)s with Different Structures, Biomacromolecules 3(4):768-774 (2002).
International Search Report of PCT/US2007/083600, mailed Nov. 5, 2008, 5 pages.
International Search Report of PCT/US2007/083605, mailed Dec. 15, 2008, 6 pages.
International Search Report of PCT/US2007/083620, mailed Dec. 5, 2008, 4 pages.
International Search Report of PCT/US2007/083634, mailed Nov. 5, 2008, 5 pages.
International Search Report of PCT/US2007/083639, mailed Dec. 12, 2008, 5 pages.
International Search Report of PCT/US2007/083642, mailed Nov. 5, 2008, 5 pages.
International Search Report of PCT/US2007/083646, mailed Dec. 15, 2008, 6 pages.

(56) References Cited

OTHER PUBLICATIONS

International Search Report of PCT/US2008/082487, mailed Feb. 27, 2009, 3 pages.
International Search Report of PCT/US2009/047751, mailed Feb. 2, 2010, 3 pages.
International Search Report of PCT/US2010/022701, mailed Mar. 31, 2010, 2 pages.
International Search Report of PCT/US2010/024004, mailed Nov. 26, 2010, 5 pages.
International Search Report of PCT/US2010/042585, mailed May 25, 2011, 8 pages.
International Search Report of PCT/US2010/047307, mailed Apr. 28, 2011, 3 pages.
International Search Report of PCT/US2010/050468, mailed Jan. 6, 2011, 3 pages.
International Search Report of PCT/US2011/028094, mailed Jul. 14, 2011, 4 pages.
International Search Report of PCT/US2011/032195, mailed Oct. 27, 2011, 3 pages.
International Search Report of PCT/US2011/041002, 4 pages (Feb. 29, 2012).
IPRP of PCT/US2007/083600, mailed May 5, 2009, 6 pages.
IPRP of PCT/US2007/083605, mailed May 5, 2009, 10 pages.
IPRP of PCT/US2007/083620, mailed May 5, 2009, 6 pages.
IPRP of PCT/US2007/083634, mailed May 5, 2009, 6 pages.
IPRP of PCT/US2007/083639, mailed May 5, 2009, 6 pages.
IPRP of PCT/US2007/083642, mailed May 5, 2009, 6 pages.
IPRP of PCT/US2007/083646, mailed May 5, 2009, 10 pages.
IPRP of PCT/US2008/082487, mailed May 11, 2010, 10 pages.
IPRP of PCT/US2009/047751, mailed Dec. 18, 2010, 5 pages.
IPRP of PCT/US2010/022701, mailed Aug. 2, 2011, 5 pages.
IPRP of PCT/US2010/024004, mailed Aug. 16, 2011, 6 pages.
IPRP of PCT/US2010/042585, mailed Jan. 24, 2012, 6 pages.
IPRP of PCT/US2010/047307, mailed Mar. 6, 2012, 5 pages.
Jiang, W. et al, Silicon and Polymer Nanophotonic Devices Based on Photonic Crystals, Proceedings of the International Society of Optical Engineering, 6124(1):612410-1(2006).
Jin, I.J. et al., Water-Stable Silk Films with Reduced Beta-Sheet Content, Adv. Funct. Mater., 15:1241-1247 (2005).
Kouba et al., Fabrication of Nanoimprint Stamps for Photonic Crystals, Journal of Physics: Conference Series, 34(1):897-903 (2006).
Lawrence et al., Bioactive silk protein biomaterial systems for optical devices, Biomacromolecules, Amer. Chem. Society, 9(4):1214-1220 (2008).
Lawrence, B.D. et al., Bioactive silk protein biomaterial systems for optical devices, Biomacromolecules, 9:1214-1220 (2008).
Min, B.M. et al., Regenerated Silk Fibroin Nanofibers: Water Vapor-Induced Structural Changes and Their Effects on the Behavior of Normal Human Cells, Macromol. Biosci., 6(4):285-292 (2006).
Minoura, N. et al., Attachment and Growth of Cultured Fibroblast Cells on Silk Protein Matrices, J. Biomed. Mater. Res. 29(10):1215-1221 (1995).
Notification of Transmittal of International Search Report and the Written Opinion of PCT/US2011/032195, mailed Oct. 27, 2011, 2 pages.
Ramanujam, P.S., Optical Fabrication of Nano-Structured Biopolymer Surfaces, Opt. Mater. 27:1175-1177 (2005).
Tu, D. et al., A ZEP520-LOR Bilayer Resist Lift-Off Process by E-Beam Lithography for Nanometer Pattern Transfer, Proceedings of the 7th IEEE Conference on Nanotechnology, 624-627 (2007).
Verma, M.K. et al., Embedded Template-Assisted Fabrication of Complex Microchannels in PDMS and Design of a Microfluidic Adhesive, Langmuir, 22(24)10291-10295 (2006).
Wang, L. et al., Fabrication of Polymer Photonic Crystal Superprism Structures Using Polydimethylsiloxane Soft Molds Journal of Applied Physics, 101(11):114316/1-6 (2007).
Written Opinion of PCT/US2007/083600, mailed Nov. 5, 2008, 5 pages.
Written Opinion of PCT/US2007/083605, mailed Dec. 15, 2008, 9 pages.
Written Opinion of PCT/US2007/083620, mailed Dec. 5, 2008, 5 pages.
Written Opinion of PCT/US2007/083634, mailed Nov. 5, 2008, 5 pages.
Written Opinion of PCT/US2007/083639, mailed Dec. 12, 2008, 5 pages.
Written Opinion of PCT/US2007/083642, mailed Nov. 5, 2008, 5 pages.
Written Opinion of PCT/US2007/083646, mailed Dec. 15, 2008, 9 pages.
Written Opinion of PCT/US2008/082487, mailed Feb. 27, 2009, 9 pages.
Written Opinion of PCT/US2009/047751, mailed Feb. 2, 2010, 4 pages.
Written Opinion of PCT/US2010/022701, mailed Mar. 31, 2010, 4 pages.
Written Opinion of PCT/US2010/024004, mailed Nov. 23, 2010, 5 pages.
Written Opinion of PCT/US2010/042585, mailed May 25, 2011, 5 pages.
Written Opinion of PCT/US2010/047307, mailed on Apr. 28, 2011, 4 pages.
Written Opinion of PCT/US2011/032195, mailed Oct. 27, 2011, 5 pages.
Xia and Lu et al., Fabrication and properties of conductive conjugated polymers/silk fibroin composite fibers, Composites Science and Technology, 68:1471-1479 (2008).
Xu, P. and Kaplan, D.L., Horseradish peroxidase catalyzed polymerization of tyrosine derivatives for nanoscale surface patterning, Journal of Macromolecular Science, Part A: Pure and Applied Chemistry, 41(12):1437-1445 (2004).
Yang, L.J. et al., Fabrication of SU-8 embedded microchannels with circular cross-section, International Journal of Machine Tools & Manufacturing, 44:1109-1114 (2004).
Kundu et al, Silk fibroin nanoparticles for cellular uptake and control release, Int'l J O Pharmaceutics, 388:242-250 (2010).

* cited by examiner

SILK TRANSISTOR DEVICES

CROSS REFERENCE TO RELATED APPLICATION

This application is a Continuation of U.S. Non-Provisional application Ser. No. 13/393,505 filed Feb. 29, 2012, which is a 35 U.S.C. §371 National Stage of International Application No. PCT/US2010/047307, entitled "Silk Transistor Devices" and filed on Aug. 31, 2010, which claims the benefit of and priority to U.S. Provisional Application No. 61/238,319 filed Aug. 31, 2009, the contents of each of which are hereby incorporated by reference in their entirety.

GOVERNMENT SUPPORT

This invention was made with government support under contract No. W911NF-07-1-0618 awarded by the U.S. Army Research Laboratory and the U.S. Army Research Office. The U.S. federal government has certain rights in the invention.

FIELD OF THE INVENTION

The invention is directed to ecosustainable and biocompatible, low cost, ambient friendly electronic or optoelectronic devices made with silk fibroin or combined with other biopolymers, methods for fabrication and methods of using thereof.

BACKGROUND OF THE INVENTION

Recently, innovative devices based on semiconductors (Rogers & Huang, 27 PNAS 10875-76 (2009); Kim & Rogers, 20 Adv. Mater. 4887-92 (2008)) have been developed. In particular, attempts have been made to use organic semiconductors as active materials for thin film transistors and in flexible electronics (Forrest, 428 Nature 911 (2004); Singh & Sariciftci, 36 Ann. Rev. Mater. Res. 199-230 (2006); Dodabalapur, 9 Materials Today 24-30 (2006); Santato et al., 86 Appl. Phys. Lett. 141106 (2005); Melpignano et al., 88 Appl. Phys. Lett. 153514 (2006)). Combining the unique properties of organic semiconducting materials, such as light weight and flexibility, to plastic substrates and low or room temperature processing, a new generation of rubbery and soft electronics may now be possible.

A constraint for a real disruptive revolution of the electronics market relies on the ecosustainability and biocompatibility of the fabricated electronic devices. This is a fundamental issue for an effective paradigm shift to a low cost highly efficient new generation of green and bio-electronic devices. Ecosustainability, biocompatibility and biodegradability in fabrication of electronic devices or optoelectronic devices enable manufacturers and consumers to move from an oil-based economy to a green-economy. As part of this paradigm shift, there is a need for replacing the plastic or other non-ecosustainable electrical or optoelectrical components with biodegradable materials for highly efficient transistor fabrication and transistor based devices. This invention answers that need.

SUMMARY OF THE INVENTION

The invention utilizes ecosustainable, biocompatible and biodegradable silk fibroin for fabrication of electronics or optoelectronics, such as transistors, light emitting transistors, diodes, light emitting diodes, capacitors, sensors, and living transistors.

On aspect of the invention relates to a silk-based electronic device comprising a substrate; at least one electrically active layer comprising an organic semiconducting material; and at least one electrical contact in contact with the active layer. The substrate supports the other components of the electronic device. In one embodiment, the substrate is a silk matrix. The detailed configurations of the silk-based electronic device may depend on the type of electronic device. For example, the electronic device may be a transistor, a diode, a light-emitting diode, a light-emitting transistor or a capacitor.

One aspect of the invention relates to a silk-based transistor, for example, a silk-based field-effect transistor or silk-based light-emitting transistor. The silk-based transistor comprises a substrate including a gate contact; a silk dielectric layer positioned over the substrate; at least one active layer comprising an organic semiconducting material positioned over the silk dielectric layer; and source and drain contacts positioned over the active layer.

Another aspect of the invention relates to a silk-based transistor. The transistor comprises a substrate including a gate contact; a silk dielectric layer positioned over the substrate; at least one active layer comprising a silk matrix doped with an organic semiconducting material positioned over the silk dielectric layer; and source and drain contacts positioned over the active layer.

Another aspect of the invention relates to a silk-based transistor embedding an electronically active biological material as an active part of the transistor. The transistor comprises a substrate including a gate contact; a dielectric layer positioned over the substrate; at least one active layer comprising a silk matrix embedded with an electronically active biological material positioned over the dielectric layer; and source and drain contacts in contact with the active layer.

Another aspect of the invention relates to methods of fabrication a silk-based electronic device. The method comprises the steps of providing an electrically active layer comprising an organic semiconducting material; and providing a substrate to support the active layer. The method may further comprise applying a dielectric layer to the substrate between the active layer and substrate. The substrate and dielectric layer may be a silk matrix or silk matrix combining with other conventional plastic materials. The method may further comprise positioning one or more electrical contact in contact with the active layer. For example, for fabrication a silk-based transistor, the method may comprise the steps of providing a substrate; forming an silk dielectric layer over the substrate; forming an electrically active layer comprising an organic semiconducting material over the silk dielectric layer; positioning source and drain contacts in contact over the active layer; and positioning gate contact between dielectric layer and substrate.

Yet another aspect of the invention relates to a method of evaluating an activity of an electronically active biological material. The method comprises the steps of providing a silk-based electronic device comprising a substrate including a gate contact, a dielectric layer positioned over the substrate, at least one active layer comprising a silk matrix embedded with the electronically active biological material positioned over the dielectric layer, and source and drain contacts in contact with the active layer; exposing the electronically active biological material to a stimulant to produce or change a parameter of the silk-based electronic device; and evaluating the activity of the biological material based on the parameter or change of the parameter of the silk-based electronic device.

Yet another aspect of the invention relates to a method of identifying an agent that modulates an activity of an electronically active biological material. The method comprises the steps of providing a silk-based electronic device comprising a substrate including a gate contact, a dielectric layer positioned over the substrate, at least one active layer comprising a silk matrix embedded with the electronically active biological material positioned over the dielectric layer, and source and drain contacts in contact with the active layer; measuring a first parameter of the silk-based electronic device; exposing the electronically active biological material to an agent; measuring a second parameter of the silk-based electronic device; and comparing the second and first parameters of the silk-based electronic device before and after the exposing step, wherein a change in parameters indicates the agent is capable of modulating the activity of the biological material.

DETAILED DESCRIPTION

Figure 1:
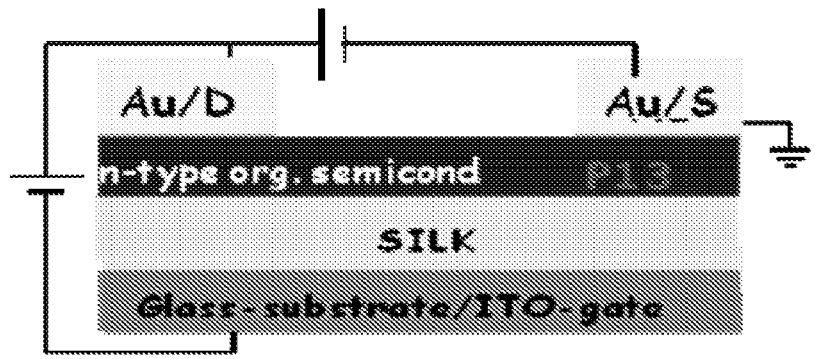
FIG. 1 is a schematic depicting a silk-based n-type transistor in top contact configuration.

The invention relates to ecosustainable and biocompatible, low cost, ambient friendly electronic and optoelectronic devices, such as transistors and light-emitting transistors, made with silk fibroin or blended with other biopolymers, methods for fabrication and methods of using the silk-based electronics and optoelectronics.

On aspect of the invention relates to a silk-based electronic device comprising a substrate; at least one electrically active layer comprising an organic semiconducting material; and at least one electrical contact in contact with the active layer. The substrate supports the other components of the electronic device. In one embodiment, the substrate is a biocompatible and biodegradable silk matrix. The active layer can be a silk matrix doped with an organic semiconducting material. The silk-based electronic device can comprise one or more active layers, with each layer comprising a same or different organic semiconducting material. Alternatively, one or more of the active layers are silk layers each doped with a same or different organic semiconducting material.

The detailed configurations of the silk-based electronic device may depend on the type of electronic device. For example, the electronic device may be a transistor, a diode, a light-emitting diode, a light-emitting transistor or a capacitor. For example, a silk-based diode may comprise a substrate; and at least one electrically active layer comprising an organic semiconducting material. The silk-based diode may also include one or more electrical contacts positioned in contact with the active layer. For a light-emitting device, the active layer may possess light-emitting properties, for example, the organic semiconducting material may be light-emitting. Alternatively, the active layer may also comprise additional light-emitting element.

One aspect of the invention relates to a silk-based transistor, for example, a silk-based field-effect transistor or silk-based light-emitting transistor. The silk-based transistor comprises a substrate including a gate contact; a silk dielectric layer positioned over the substrate; at least one active layer comprising an organic semiconducting material positioned over the silk dielectric layer; and source and drain contacts positioned over the active layer.

Some embodiments of the invention relate to high field-effect mobility silk organic film transistors. Silk-based electronics demonstrates the ability to fabricate a new generation of ecosustainable, biodegradable, and flexible devices. Silk fibroin can be integrated to electronic devices enabling living cell activity together with electrical characterization and optical imaging. The silk organic transistors may also be used to generate silk-organic light emitting diodes or a silk organic light emitting transistors. Plastic can be substituted with a protein for applications in flexible (organic) electronics and bioactive and biocompatible sensors and transistors, with illuminators optically integrated. These types of systems can be used in medical implants or environmental-friendly device.

Figure 9:
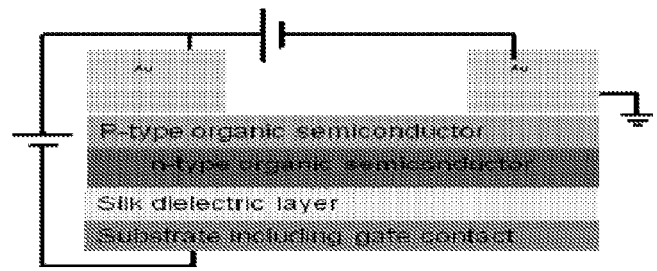
FIG. 9 is a schematic depicting a configuration of silk-based transistor combining in a multilayer structure n- and p-type silk based transistors.
Figure 10:
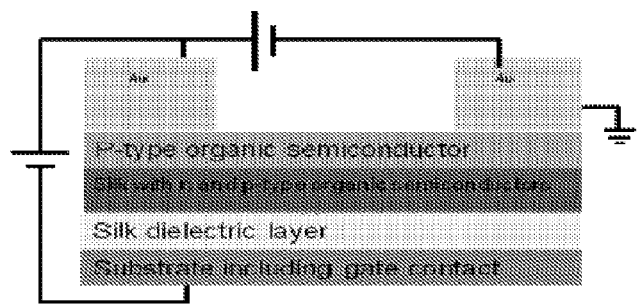
FIG. 10 is a schematic depicting a configuration of silk-based transistor combining n-p-type silk doped to a p-type silk-based transistor with a silk dielectric layer.

Silk-based electronic devices, such as the exemplified n-, p- or n-p-type silk-based transistors, may be fabricated both in a multilayer structure or in a silk-doped matrix. Schematics of non-limiting configurations for silk-based transistors are illustrated in FIG. 9, and FIG. 10.

Silk-Based Transistors

One embodiment of the invention relate to silk-based electronic device, such as silk organic film transistor. For example, silk fibroin films were exploited for high mobility silk-based organic film transistors, including a Field Effect Transistor (OFET).

Exemplary configurations of silk-based transistor include a silk fibroin, in gel or uncross-linked film or cross-linked film or crystalline form, combined with organic semiconducting materials in a layered or multilayered field effect transistor architecture, thereby forming high-efficient film transistors in both unipolar (p- or n-type) and ambipolar (p-n-type) configurations, one or more electrical contacts and a substrate supporting the transistor.

Silk fibroin can act as an optically transparent, biodegradable, and bioactive dielectric layer. Silk fibroin can also act as an optically transparent, biocompatible and biodegradable substrate. Silk fibroin can also be combined with plastics to make dielectric layer or substrate. Exemplary plastics include Polyethylene terephthalate (PET), Polyvinyl alcohol (PVA), Polycarbonate (PC), Poly(methyl methacrylate) (PMMA), Poly(lactic-co-glycolic acid) (PLGA) or Polyhydroxybutyrate (PHB).

The silk-based transistor can be made conformable and/or edible. For example, the active layer of the silk-based transistor can be prepared as silk matrix doped with organic semiconducting materials to form high efficient film transistors in both unipolar (p- or n-type) and ambipolar (p-n-type) configurations.

Transistors made using the method of the invention may be used to amplify or switch electronic signals. When a voltage or current is applied to a pair of the transistor's terminals, the silk fibroin provides an organic semiconductor material that alters the current flowing through the other pair of terminals. The output signal and power may be altered and controlled based upon the input signals. As such, the silk-based transistors may provide amplification and switching capabilities.

Silk-Based Light-Emitting Transistors

Organic light-emitting transistors (OLETs) (Muccini, 5 Nature Mater. 605-13 (2006); Hepp et al., 91 Phys. Rev. Lett. 157406 (2003); Rost et al., 85 Appl. Phys Lett. 1613-15 (2004); Zaumseil et al., 5 Nature Mater. 69-74 (2006); Santato et al., 86 Appl. Phys. Lett. 141106 (2005)) have the ability to combine the advantages and functions of a transistor with electroemission in a single device. Moreover, electroemission efficiency and nanolocalization of the light emission make OLETs a multifunctional device concept. Plastic-based fabrication of OLETs makes flexible optoelectronic devices possible. It is believed that this is the first example of an ecosustainable, biocompatible, and bioactive OLET.

One embodiment of the invention relates to a silk-based electronic device, such as silk organic light emitting transistor. Exemplary configurations of silk organic light emitting transistor include a silk fibroin, in gel or uncross-linked film or cross-linked film or crystalline form, combined with organic semiconducting light emitting materials in a layered or multilayered field effect transistor architecture, thereby forming high efficient light-emitting transistors, one or more electrical contacts and a substrate supporting the transistor. The kind of the silk-based light-emitting transistor can be unipolar (p- or n-type) or ambipolar (p-n-type).

Silk fibroin can act as an optically transparent, biodegradable, and bioactive dielectric layer. Silk fibroin can also act as an optically transparent, biocompatible and biodegradable substrate. Silk fibroin can also be combined with plastics to make dielectric layer or substrate. Exemplary plastics include Polyethylene terephthalate (PET), Polyvinyl alcohol (PVA), Polycarbonate (PC), Poly(methyl methacrylate) (PMMA), Poly(lactic-co-glycolic acid) (PLGA) or Polyhydroxybutyrate (PHB).

Figure 18:
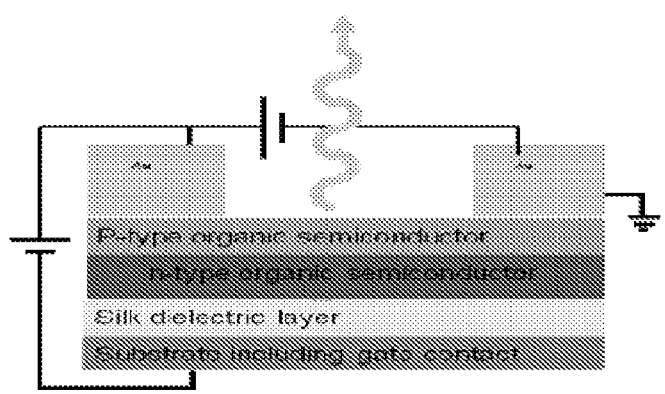
FIG. 18 is a schematic depicting a configuration of silk-based light emitting transistor combining in a multilayer structure.

Typically, all the configurations described for silk-based transistors can be transferred to silk-based light emitting transistors, when light emitting elements are contained in the silk-based transistors. For example, silk-based light-emitting transistors, such as the exemplified n- or p- (unipolar) or n-p-type (ambipolar) silk based light-emitting transistors, may be fabricated both in a multilayer structure or in a silk-doped matrix, for instance, as shown in FIG. 18. Organic light emitting semiconducting materials can be deposited as single layer or engineered multilayer n-p-type and light emitter interfaced to silk film or combined as n-p-type into silk matrix. The electro-radioactive emission can occur via direct recombination of electron-holes into a transport/emitting organic moiety or by energy transfer in an engineered multilayer structure.

The silk-based light-emitting transistor can also be n- or p-type (unipolar) or n-p-type (ambipolar) and fully biocompatible, edible, implantable, and resorbable in vivo and in vitro for bio-diagnostic and biomedical applications, and applied as green electronics and optoelectronics in a variety of fields, such as in the food industry, packaging, agriculture, general electronics, optoelectronics, and security. The multifunctional device can supply electronic switching together with localized nanometer scale light emission for photoactivation of drugs or biosystems, lighting and/or all the functions related to lighting systems.

Silk-Based Diodes and Light-Emitting Diodes

Silk-based electronic device can be made in different type of configurations. In one embodiment, provided herein is a silk-based organic diode or organic light-emitting diode (OLED).

Exemplary configuration of silk-based diode comprises a substrate; and at least one electrically active layer comprising an organic semiconducting material. The silk-based diode may also include one or more electrical contacts positioned in contact with the active layer.

Similarly as embodiments described for silk-based transistors, for silk-based diode, silk fibroin can act as an optically transparent, biocompatible and biodegradable substrate. Silk fibroin can also be combined with plastics to make the substrate. Exemplary plastics include PET, PVA, PC, PMMA, PLGA or PHB. The silk-based diodes can be made conformable and/or edible. For example, the active layer of the silk-based diode can be prepared as silk matrix doped with organic semiconducting materials to form diodes in both unipolar (p- or n-type) and ambipolar (p-n-type) configurations.

For a light-emitting diode, the active layer may possess light-emitting properties, for example, the organic semiconducting material may be light-emitting. Alternatively, the active layer may also comprise additional light-emitting element.

Silk-Biological Material Based Electronic Device

In another embodiment, a silk-based electronic device is fabricated containing silk-matrix embedded with excitable cells, tissues or organism as an active part of the electronic device.

For example, provided herein is a silk-based transistor using silk-matrix hosting cells as an active part of the device. Primary cell activity, including astrocytes, on silk-based transistor device, provides a full cycle of utility for such systems. The system and method of the invention fulfills a green chemistry goal, generates functional organic devices, and provides biological interfaces, all empowered by the mechanical, biological and processing features of the silk protein.

The silk-biological material based electronic device shares some common technical features with the silk-organic film transistors discussed above. For example, a transparent glass substrate with ITO acting as a gate contact and source-drain gold contact may be used. The "active" part of the device, however, may be a silk-matrix (e.g., silk gel) hosting excitable biological materials, such as primary astroglial cells. The dielectric layer or substrate of the device may be a silk layer or other standard dielectric layer or substrate such as a standard PET, PVA, PC, PMMA, PLGA or PHB films.

As defined herein, "active layer" refers to active part of the electronic device that is electrically active. For example, the silk-based electronic device may include an active layer comprising organic semiconducting material for electron conduction. Alternatively, the active layer may also contain electronically excitable biological material for controllable electron conduction.

Organic semiconducting moieties may be used in the active layer for electron conduction. Exemplary organic semiconducting materials include thiophene derivatives, perylene derivatives, fluorine derivatives, or phenyl derivative, and etc. In one embodiment, biocompatible and water-soluble organic semiconducting materials are used in the active layer, such as the commercially available thiophene derivates both available in n-type or p-type. Since silk fibroin is a water-soluble biomaterial, the advantages of the usual hydrophobic behavior of common standard organic semiconducting systems may be capitalized upon. For example, the organic semiconducting material can be doped in the water soluble silk fibroin to form an active layer comprising silk matrix doped with organic semiconducting materials.

When fabricated and used as light-emitting transistor or diode, the organic semiconducting material in the active layer may confer light-emitting properties to the transistor or diode. Alternatively, additional light-emitting elements may be added to the active layer. Exemplary light-emitting materials that may be added into the active layer include organometallic complexes (such as Ir and Pt complexes), organic dyes, semiconducting quantum dots, metal nanoparticles, and etc.

The active layer of the silk-based electronic device may be a layer containing organic semiconducting moieties that present n-type, n-type or p-n junction properties. The active part of the silk-based electronic device can also be a combination of multilayers. For example, the multilayer can be a combination of layers containing organic semiconducting moieties presenting the same or different charge transport and/or light-emitting properties. For example, organic light emitting semiconducting materials can be deposited as single layer or engineered multilayer n-p-type and light emitter interfaced to silk matrix or combined as n-p-type into silk matrix. The electro-radioactive emission can occur via direct recombination of electron-holes into a transport/emitting organic moiety or by energy transfer in an engineered multilayer structure.

In addition to vacuum deposition techniques, the n-, p- or n-p-type electronic device or light-emitting device may be fabricated in many other techniques known by skilled in the art, such as by spin-coating, dipping, or casting techniques.

Electrical contacts (such as gate, source or drain contact), or electrodes, included in all configurations of the silk-based electronic device (e.g., top or bottom source-drain and buried or top or bottom gate), include conductive materials, such as metal, metal oxide, or electrically conductive polymer. For example, electrical contacts can be metal contacts, such as biocompatible gold, copper, iron, aluminum, or transparent metal oxide such indium-tin-oxide. Electrical contacts used herein can also be a biocompatible and/or biodegradable electrically conducting polymers, melanin, aromatic amino acids and their oligomers/polymers, porphyrin based proteins, metalized biopolymers, poly(pyrrole), polyaniline, polyacetyline, poly-p-phenylene, poly-p-phenylene-vinylene, polythiophene, or hemosin. See also, WO 2008/085904.

All components of silk-based electronic device may be biocompatible materials. In some embodiments, at least some components of silk-based electronic device are bioresorbable (e.g., water soluble) or biodegradable, therefore photonic adds electrical and/or electro-optical functionalities to living tissue or organism without need for retrieval.

Additionally, the material properties of silk allow for the coexistence of electronic and/or electro-optical functions and biological storage, leading to multifunctional electronic or electro-optical systems where functionalities, such as drug/therapeutic delivery, can also be incorporated into the implanted electronic or optoelectronics device. The lack of need to retrieve the devices extends the utility of this material platform beyond medical applications into environmental monitoring or food chain safety where such devices can be used without negative impact on the environment or the consumer.

The silk-based transistors or diodes are multifunctional and multipurpose and may have a variety of both extracorporeal and corporeal applications and uses. The silk-based transistors or diodes can be implanted in vivo and in vitro for biomedical applications without having to retrieve the device since the devices may be completely and/or partially resorbable, bioactive and not harmful for in vivo systems.

The silk-based devices may be used in the field of drug discovery. More specifically, the silk-based transistors or diodes of the invention provides for drug screening assays and devices that are used to identify agents or test the effect of the agents on activities of cells, tissues or organs. For example, silk matrices of the transistors may comprise cells, tissues or organs that are excitable.

The silk-based devices may be used in the food industry and embedded in packaging for tracking and sensing, for security purposes or exploited as disposable not harmful for the environment efficient general electronics and optoelectronics devices.

It can also be desirable to design a bio-integrated device, such as an implantable medical device, which has a large fraction of the device flexible to easily conform to the surface of a subject to be contacted with the implantable medical device. For example, the silk-based device may be fabricated on an ultrathin and flexible substrate, such as silk substrate. The active organic semiconducting material can also be doped in flexible silk matrix. Such implantable devices can hence form conformal contact with the curvilinear surfaces of various organs or tissues.

Silk Matrix

Biopolymers, especially silk proteins, present novel structure and resulting functions. For example, from a materials science perspective, silks spun by spiders and silkworms represent the strongest and toughest natural fibers known and present various opportunities for functionalization, processing, and biocompatibility. Silk-based materials achieve their impressive mechanical properties with natural physical crosslinks of thermodynamically stable protein secondary structures also known as beta sheets ($\beta$-sheets). Thus, no exogenous crosslinking reactions or post-processing crosslinking is required to stabilize the materials. The presence of diverse amino acid side chain chemistries on silk protein chains facilitates coupling chemistry to functionalize silks, such as with cytokines, morphogens, and cell binding domains. There are no known synthetic or biologically-derived polymer systems that offer this range of material properties or biological interfaces, when considering mechanical profiles, aqueous processing, ease of functionalization, diverse modes of processing, self-forming crosslinks, biocompatibility, and biodegradability.

Silk, contained in the electronic device of the invention, has been demonstrated to be an excellent material for fabrication of silk optical elements such as refractive and diffractive lenses, gratings, photonic band gap structures, holograms, optical fibers and microfluidic devices. Moreover, silk is biocompatible, already used in medical sutures and can be utilized as a drug release medium. Wiltz et al., 29 Biomaterials 3609-16 (2008). Silk degradation can be controlled in a lifetime range from weeks to years depending upon the mode of processing.

As used herein, the term "fibroin" includes silkworm fibroin and insect or spider silk protein (Lucas et al., Adv. Protein Chem 13: 107-242 (1958)). Preferably, silk fibroin is obtained from a solution containing a dissolved silkworm silk or spider silk. The silkworm silk protein is obtained, for example, from *Bombyx mori*, and the spider silk is obtained from *Nephila clavipes*. In the alternative, the silk proteins suitable for use in the invention can be obtained from a solution containing a genetically engineered silk, such as from bacteria, yeast, mammalian cells, transgenic animals or transgenic plants. See, for example, WO 97/08315 and U.S. Pat. No. 5,245,012.

An aqueous silk fibroin solution may be prepared from the silkworm cocoons using techniques known in the art. Suitable processes for preparing silk fibroin solution are disclosed in, for example, U.S. patent application Ser. No. 11/247,358, WO/2005/012606, and WO/2008/127401. In one embodiment, *B. mori* cocoons are boiled for about 30 minutes in an aqueous solution. The aqueous solution may be 0.02 M sodium carbonate. The cocoons are rinsed with water to extract the sericin proteins and the extracted silk is dissolved in an aqueous salt solution. Salts useful for this purpose include, but not limited to, lithium bromide, lithium thiocyanate, calcium nitrate or other chemicals capable of solubilizing silk. For example, the extracted silk may be dissolved in about 9-12 M LiBr solution at 60° C. for 4 hours, yielding a 20% (w/v) solution. The salt is consequently removed using dialysis. The solution maybe centrifuged to remove small amounts of silk aggregates that may form during the process, usually from environment contaminants that are present on the cocoons. The final concentration of silk fibroin aqueous solution may be approximately 5-20% (w/v). To obtain a silk fibroin solution with a higher concentration, the silk fibroin solution with a lower concentration may be dialyzed against a hygroscopic polymer, for example, PEG, a polyethylene oxide, amylose or sericin. For example, an 8% silk fibroin solution may be dialyzed against 10% (w/v) PEG (10,000 g/mol) solution. The dialysis is for a time period sufficient to result in a final concentration of aqueous silk solution between 10-30%. Typically dialysis for 2-12 hours is sufficient.

The silk aqueous solution can then be processed into silk matrix with desired shapes or formats, such as silk hydrogels, films, conformal coatings or layers, foams, sponges, 3-dimensional porous scaffolds or solid blocks, or fibers, for further processing into the silk-based transistors. Silk film, for example, can be micro and nano-patterned and imprinted with processing and manipulation carried out under ambient conditions. Free-standing silk films with an area of 40 cm$^2$ have been fabricated with high optical quality and transparency in the visible range.

Silk hydrogels can be prepared by methods known in the art. For example, the gelation of silk fibroin solution can be induced by changes in silk fibroin concentration, temperature, salt concentrations, pH, adding hydrophilic polymers, applying sonication, vortexing, and the like. Suitable processes for preparing silk hydrogel are disclosed in, for instance, WO/2005/012606 and WO/2008/150861. The resulting silk hydrogels can then be cut into any shape, using, for instance, a laser.

Silk films or silk coatings or layers can be prepared by casting the aqueous silk fibroin solution on the substrate. Casting of the silk films can be performed using any known means, e.g. a spin-coating method, where the silk solution is spin coated onto the substrate to allow the fabrication of thin membranes of non-uniform in height; or simply by pouring silk fibroin solution over the top of the substrate. Single layer or multiple layers of silk films may be casted on the substrate. The thickness of the films or coatings may be controlled changing the concentration, or volumes of silk solution or by depositing different numbers of layers. Suitable processes for preparing silk films or silk layers are disclosed in, for example WO 2005/012606, WO/2006/042287, and WO/2007/016524.

Silk foams may be made from methods known in the art, including, for example, freeze-drying and gas foaming in which water is the solvent or nitrogen or other gas is the blowing agent, respectively. Alternately the foam is made by contacting the silk fibroin solution with granular salt. Suitable processes for preparing silk hydrogel are disclosed in, for example WO 2005/012606.

Silk matrix of the invention may also be a 3-dimensional silk scaffold, prepared by means known in the art. For example, silk scaffold can be produced using a molding process. Typically, silk solution is placed into a mold, the mold being a negative of the desired shape of the scaffold. The solution is cured and removed from the mold. See, for example, WO 03/004254, WO 03/022319 and WO 04/000915.

Silk fibers may be prepared by methods known in the art, for example, by processing the aqueous silk fibroin solution to form a fiber. Exemplary processing methods include, but not limited to, electrospinning, wet spinning, or pulling the fibers directly from the solution. Suitable processes for preparing silk fibers are disclosed in, for example U.S. Pat. No. 6,902,932, US Patent Publication 2005/0089552, WO 2004/0000915, or WO 2005/012606. Additionally, silk fiber having optical quality can also be prepared from by drawing fibers from viscous silk gel. See, also, U.S. Patent Application No. 61/246,323.

The conformation of the silk matrix may be altered (e.g., conformation conversion between random coil, silk I conformation and silk II conformation, etc.) by methods known in the art. For example, the conformation of the matrix may be altered to increase the crystallinity or liquid crystallinity by contacting the fibroin matrix with alcohol (such as methanol) or salt, or by applying sheer stress, electric field, pressures, and so on.

Other biocompatible and biodegradable polymers may be blended in the silk matrix for fabrication of silk-based electronic device. For example, additional biopolymers, such as chitosan, exhibit desirable mechanical properties, can be processed in water, blended with silk fibroin, and form generally clear films for optical applications. Other biopolymers, such as chitosan, collagen, gelatin, agarose, chitin, polyhydroxyalkanoates, pullan, starch (amylose amylopectin), cellulose, alginate, fibronectin, keratin, hyaluronic acid, pectin, polyaspartic acid, polylysin, pectin, dextrans, and related biopolymers, or a combination thereof, may be utilized in specific applications, and synthetic biodegradable polymers such as polyethylene oxide, polyethylene glycol, polylactic acid, polyglycolic acid, polycaprolactone, polyorthoester, polycaprolactone, polyfumarate, polyanhydrides, and related copolymers may also be selectively used. The polymer selected herein to be blended into the silk films should not negatively impact the stability, electrical property and/or optical quality of silk matrix.

Additionally, the silk-based electronic device of the invention may also be biologically activated by incorporating small organic materials. In particular, the silk matrices can be biologically functionalized by embedding with one or more organic indicators, living cells, organisms, markers, proteins, and the like. More specifically, the silk matrix may be embedded or coated with organic materials such as red blood cells, horseradish peroxidase, phenolsulfonphthalein, nucleic acid, a dye, a cell, an antibody, enzymes, for example, peroxidase, lipase, amylose, organophosphate dehydrogenase, ligases, restriction endonucleases, ribonucleases, DNA polymerases, glucose oxidase, laccase, cells, viruses, proteins, peptides, small molecules (e.g., drugs, dyes, amino acids, vitamins, antioxidants), DNA, RNA, RNAi, lipids, nucleotides, aptamers, carbohydrates, chromophores, light emitting organic compounds such as luciferin, carotenes and light emitting inorganic compounds (such as chemical dyes), antibiotics, antifungals, antivirals, light harvesting compounds (such as chlorophyll, bacteriorhodopsin, protorhodopsin, and porphyrins), and electronically active compounds, tissues or other living materials, other compounds or combinations thereof. The embedded materials are biologically active, thereby adding biological functionality to the resultant silk based devices. At least one active agent may be added into silk matrix. Active agent may be added into the silk fibroin solution before or during the processing of silk fibroin solution into silk matrix.

In some embodiments, the active agent may also be an organism such as a fungus, plant, animal, bacterium, or a virus (including bacteriophage). Moreover, the active agent may include neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

Exemplary cells suitable for use herein may include, but are not limited to, progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, and precursor cells. The active agents can also be the combinations of any of the cells listed above. See also WO 2008/106485; PCT/US2009/059547; WO 2007/103442.

Exemplary antibodies that may be incorporated in silk fibroin include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab. The active agents can also be the combinations of any of the antibodies listed above.

Exemplary antibiotic agents include, but are not limited to, actinomycin; aminoglycosides (e.g., neomycin, gentamicin, tobramycin); β-lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxacillin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics. Optionally, the antibiotic agents may also be antimicrobial peptides such as defensins, magainin and nisin; or lytic bacteriophage. The antibiotic agents can also be the combinations of any of the agents listed above. See also PCT/US2010/026190.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like. Interactions between components may also be used to functionalize silk fibroin through, for example, specific interaction between avidin and biotin. The active agents can also be the combinations of any of the enzymes listed above. See PCT/US2010/042585.

When introducing therapeutic agents or biological material into the silk matrix, other materials known in the art may also be added with the agent. For instance, it may be desirable to add materials to promote the growth of the agent (for biological materials), promote the functionality of the agent after it is released from the silk film, or increase the agent's ability to survive or retain its efficacy during the period it is embedded in the silk. Materials known to promote cell growth include cell growth media, such as Dulbecco's Modified Eagle Medium (DMEM), fetal bovine serum (FBS), non-essential amino acids and antibiotics, and growth and morphogenic factors such as fibroblast growth factor (FGF), transforming growth factors (TGFs), vascular endothelial growth factor (VEGF), epidermal growth factor (EGF), insulin-like growth factor (IGF-I), bone morphogenetic growth factors (BMPs), nerve growth factors, and related proteins may be used. Growth factors are known in the art, see, e.g., Rosen & Thies, CELLULAR & MOLECULAR BASIS BONE FORMATION & REPAIR (R.G. Landes Co., Austin, Tex., 1995). Additional options for delivery via the silk include DNA, siRNA, antisense, plasmids, liposomes and related systems for delivery of genetic materials; peptides and proteins to activate cellular signaling cascades; peptides and proteins to promote mineralization or related events from cells; adhesion peptides and proteins to improve film-tissue interfaces; antimicrobial peptides; and proteins and related compounds.

Alternatively, the silk fibroin may be mixed with hydroxyapatite particles, see PCT/US08/82487. As noted herein, the silk fibroin may be of recombinant origin, which provides for further modification of the silk such as the inclusion of a fusion polypeptide comprising a fibrous protein domain and a mineralization domain, which are used to form an organic-inorganic composite. These organic-inorganic composites can be constructed from the nano- to the macro-scale depending on the size of the fibrous protein fusion domain used, see WO 2006/076711. See also U.S. patent application Ser. No. 12/192,588.

Silk fibroin can also be chemically modified with active agents in the solution, for example through diazonium or carbodiimide coupling reactions, avidin-biodin interaction, or gene modification and the like, to alter the physical properties and functionalities of the silk protein. See, e.g., PCT/US09/64673; PCT/US10/41615; PCT/US2010/042585; Ser. No. 12/192,588.

The silk-based electronic device comprising active agents or biological materials may be suitable for long term storage and stabilization of the cells and/or active agents. Cells and/or active agents, when incorporated in silks, can be stable (i.e., maintaining at least 50% of residual activity) for at least 30 days at room temperature (i.e., 22° C. to 25° C.) and body temperature (37° C.). Hence, temperature-sensitive active agents, such as some antibiotics, can be stored in silk matrix without refrigeration. Importantly, temperature-sensitive bioactive agents can be delivered (e.g., through injection) into the body in silk matrix and maintain activity for a longer period of time than previously imagined. See, e.g., PCT/US2010/026190.

Drug Discovery and Screening

One aspect of the invention relates to the field of drug discovery. More specifically, the silk-based electronic device is used in drug screening assays and devices to identify agents or test the effect of the agents on activities of biological materials, such as the electronically active biomaterials. In this regard, silk matrix of the silk-based electronic devices may comprise electronically active biomaterials, for example, living cells, tissues, or organisms that are excitable.

"Electrically active" biological materials, as defined here, refer to biological materials that can spontaneously create an electric signal or ionic signal, or can be stimulated to create an electric signal or ionic signal, for instance. For instance, electrically active biological materials may be excitable cells, tissues or organisms. Exemplary cells include, but not limited to kidney cells, nerve cells, cardiac cells, muscle cells and secretory cells. An excitable cell typically has ion channels. Tissues are ensemble of cells, not necessarily identical, but from the same origin. Excitable tissues hence may include ensembles of excitable cells, as well as sensory receptors, axons, and muscle fibers. Excitable cells in tissues (e.g., nervous, brain, cardiac, or muscular tissue) can be modulated or excited by electric fields, providing a possible therapeutic approach for several disorders affecting these tissues.

The silk-based electronic devices can be used with any type of cell, or combination thereof, including animal cells, plant cells, insect cells, bacterial cells, yeast and mammalian cells. For screening for human therapeutics, mammalian cells may be used. The cells may be derived from tissue, primary culture, stem cell derived cell lines including iPS cells, or tissue culture origin. For example, cells may be derived from embryonic tissues. Exemplary cell type used in the invention may be a neuronal cell type, for example, hippocampal cells; or a non-neuronal cell type, for example, glial cells.

One embodiment of the invention relates to a screening method to identify agents that can modulate cell, tissue, or organism activities or functionalities. Particularly, the methods of the invention allow the ability to modulate the activity of living cells, tissues or organisms without damaging cell, tissue and organism. By providing the ability to externally modulate the electric current or transmembrane potential of living cells, the invention enables a wide variety of cells, tissues or organisms to be assayed. In one embodiment, the silk-based electronic device embedding living cells, tissues or organisms can be contacted with a test agent; and the effect, if any, of the test agent on a parameter associated with normal or abnormal tissue or cell function, such as neuron response to a stimulus, or muscle contractibility, is determined. Such parameters include, but are not limited to, muscle contraction, expression of a cell-specific marker, electric signals associated with cell and tissue activity, and the like.

Accordingly, one aspect of the invention relates to a use of the silk-based electronic device embedding living cells, tissues or organisms, in assays to identify agents which affect (i.e. increase or decrease) the activity of the cells, tissues or organisms in the presence of the agent as compared to a control agent, or the absence of an agent. For example, when using a cardiac tissue, such an assay is useful to identify an agent which has a cardiotoxic effect, such as an agent which decreases contractile force, and/or cardiomyocyte atrophy, and/or results in another dysregulation of contractibility, such as arrhythmia or abnormal contraction rate.

Once identified, candidate agents can be evaluated for selectivity and toxicological effects on cells or tissues. In one embodiment, the silk-based electronic device is useful for in vitro assays and screening to detect agents that are active on the embedded cells, tissues or organisms, for example, to screen for agents that affect the differentiation of muscle cells.

Another embodiment of the invention relates to methods of screening for agents that have an adverse effect on cells, tissues or organisms, or are toxic to a cell, tissue or an organism. For example, the silk based electronic device can be used for screening the effects of the candidate drug on electrically excitable tissues such as heart or neuronal tissues, or immortalized cell cultures derived from these tissues. These tissues play critical roles within an organism and any undesired effect of the candidate drug on the ability of these tissues to be electrically stimulated would be predicted to create potential serious side effects when administered. As a consequence, active compounds that also impaired the ability of these tissues to function could be eliminated from consideration as a drug candidate at an early stage, or have medicinal chemistry performed to reduce the side effects.

In some embodiments, an agent (such as a drug or compound) to be screened can be an existing agent. In other embodiments, an agent to be screened can be new or modified agent of an existing agent (i.e. a modified drug or compound or variant thereof). By way of an example, a screening assay using silk-based electronic device embedding cardiac tissues may be useful to identify an agent which has a cardiotoxic effect by increasing contractile force and/or other types of dysregulation such as an increase in contraction rate and could lead to the development of cardiac muscle hypertrophy. These toxicity studies provide the basis for determining the therapeutic utility of a candidate agent in vivo.

The embodiments of the invention may also provide a rapid method of determining the specificity of the candidate agent. For example, a screening assay using the silk based electronic device comprising cells containing related ion channel family members can be used to rapidly profile the selectivity of a test agent with respect both to its ability to inhibit related ion channels, and their relative ability to modulate different voltage dependent states of the ion channels. Such a system provides the ability to rapidly profile large numbers of test agents in order to systematically evaluate the ion channel selectivity of a candidate drug in a simple, miniaturized high throughput format.

The screening method using silk-based electronic device embedding living cells, tissues or organisms in assays can also be used to study a disease associating with the cells, tissues or organisms. By way of an example, a tissue can comprise genetically modified cells, for example a cell carrying a mutation, polymorphism or other variant of a gene (i.e. increased or decreased expression of a heterologous gene) which can be assessed to see the effects of such a gene variant on the physiological functionality of the tissue, for example, the neuron transmission or muscle contraction. Such a tissue comprising genetically modified cells can also be used to identify an agent which attenuates (i.e. decreases) any dysfunction in physiological functionality as a result of the genetically modified cells, or alternatively can be used to identify an agent which augments (i.e. increases) any dysfunction in physiological functionality as a result of the genetically modified cells.

In the use of a silk-based electronic device embedding cells, tissues or organisms for the screening methods, a silk-based electronic device is contacted with an agent of interest, and the effect of the agent is assessed by monitoring output parameters, such as electric signals associated with cell and tissue activity output from the silk-based electronic device, force of contraction of the muscle cells, and the like.

Monitoring methods can also include measuring parameters with other physiological changes of cells and tissues. For example, optical monitoring may be combined when the effect of agents on cells, tissues or organisms associate with the change of optical properties of cells, tissues or organisms. For example, laser scanning confocal microscope may be used to detect the light emission signal change of cells associated with the cell activity before and after an electric stimulus. In one embodiment, dye molecules, such as fluorescent dyes, may be added to the cells for detection purposes. In some embodiments, additional monitoring can be performed, such as alteration of the phenotype of the cells or tissues, including but not limited to, e.g. changes in expression of cell-specific markers, cell viability, differentiation characteristics, multipotentcy capacity and the like.

Parameters are quantifiable components of cells, tissues or organisms, particularly components that can be accurately measured, desirably in a high throughput system. A parameter can be any measurable parameter related to functionality or activity of the cells, tissues or organisms as disclosed herein. Such parameters include, but are not limited to, electric signals associated with cell, tissue, or organism activity, such as voltage change or electric current that may be output from the silk-based electronic device, contractile force, frequency of contraction and the like. Other parameters include changes in characteristics and markers of the cells or tissues, and/or a change in the cell phenotype, including but not limited to changes in cell markers, cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While parameters typically related to functionality of the cells, tissues or organism provide a quantitative readout, in some instances a semi-quantitative or qualitative result will also be acceptable. Readouts can include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

In one embodiment of the invention, cell activity may be evaluated by measuring ion channel activity of cells, which could refer to the change of state of a cell through opening or closing of its ion channels. For example, the electrical elements of nerve cells are voltage-gated ion channels, which are molecules embedded in the lipid bilayer of the cell membrane. The ion channels can be in an open and in a closed state: when they are open, they selectively transmit ionic current through the membrane—Na+inward current or K+outward current. The opening and closing of the channels are connected with a displacement of electrical charge (voltage) across the membrane. The term "cellular activity" or "cell activity" means basic cell metabolism. The term "ion channel activity" means a change in state of an ion channel that allows it to alter its ion permeability. The terms "cell stimulation" or "cell excitation" mean the depolarization of a cell, such as may be achieved by destroying its membrane potential.

A drug may modulate activity of a cell by changing aspects of its ion channel function. Ion channel activity of stimulated cells, may be measured through the electric current or transmembrane potential of the cells. Additional detection method may involve using of one or more fluorescent dyes, added to the cells for detection purposes. When the cells have added fluorescent dye, the detection may, for example, detect a change in fluorescence over time.

Hence in one embodiment, a parameter used in the invention to monitor the effect of agents on cells, tissues or organisms in the screening method may be the change of electric current or voltage of ion channels in the cell. Because of the high sensitivity, the silk-based electronic device has the ability to modulate the voltage dependent state of an ion channel, which has advantages for drug discovery where it provides the opportunity to screen for compounds that interact preferentially with one state, (i.e. use-dependent blockers). For example, several known therapeutically useful drugs (including anti-arrhythmics, anti-convulsants, and local anesthetics) are known to function as use-dependent blockers of voltage-dependent sodium and/or calcium channels. In each case, total blockade of the targeted channel would typically result in death. Certain conditions, such as chronic pain, arrhythmia, and convulsions occur when cells become over-active. These conditions can be alleviated or eliminated by blocking the channels if they begin to open too often. Agents that are capable of blocking the channel, but which bind preferentially to the activated or inactivated states(s) rather than the resting state(s), can reduce the excitability of muscle and neurons. These drugs are effective because they do not affect the channel under normal circumstances, but block it only when necessary to prevent hyper-excitability. However existing methods of analysis that are compatible with high throughput screening do not provide the ability to routinely control the activation state of the ion channel in real time. In this regard, the screening method of the invention also provides for screening the effect of an agent on an ion channel in a defined functional state within a cell. The method involves modulating the transmembrane potential of the cell via the use of repetitive stimulation to cycle the ion channel of interest through its activation cycle and to set the transmembrane potential to a desired level suitable for a specific activation state, or transition between states. Then, during or after this process an agent is added to the cell, and the transmembrane potential is measured.

The agent used in the screening method as disclosed herein can be selected from a group of a chemical, small molecule, chemical entity, nucleic acid sequences, an action; nucleic acid analogues or protein or polypeptide or analogue of fragment thereof. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof. An agent can contact the surface of the cells or tissues to induce its effects. Alternatively, an agent can be intracellular within the cells as a result of introduction of a nucleic acid sequence into a cell and its transcription to result in the expression of a nucleic acid and/or protein agent within the cell.

An agent as used herein also encompasses any action and/or event or environmental stimulus that a cell, tissue or organism is subjected to. As a non-limiting examples, an action can comprise any action that triggers a electrophysiological change in the cell, for example but not limited to, electrical impulse (including increase or decrease in stimuli frequency and/or stimuli intensity), pressure, stretch, chemical transmitters, changes of the electric potential across the cell membrane, heat-shock, ionizing irradiation, cold-shock, mechanical stretch, hypoxic conditions, light and/or wavelength exposure, UV exposure, increased and/or decreased oxygen exposure, exposure to reactive oxygen species (ROS), ischemic conditions, fluorescence exposure, sensory stimuli, such as touch, odor, sound, light and numerous other stimuli affecting cells of the sensory organs, etc. Environmental stimuli also include intrinsic environmental stimuli defined below.

The exposure (i.e. contacting) of a silk-based transistor embedding cells and tissues to an agent may be continuous or non-continuous. In some embodiments, where the exposure (i.e. contacting) of a silk-based transistor embedding cells and tissues to agent is a non-continuous exposure, the exposure to one agent can be followed with the exposure to a second agent, or alternatively, by a control agent (i.e. a washing step). In some embodiments, silk-based transistor embedding cells and tissues can be exposed to at least one agent, or at least 2, or at least 3, or at least 4, or at least 5, or more than 5 agents at any one time, and this exposure can be continuous or non-continuous, as discussed above.

The term "agent" refers to any chemical, entity or moiety, including without limitation synthetic and naturally-occurring non-proteinaceous entities. In certain embodiments the compound of interest is a small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

In some embodiments, the agent is a human virus (Hepatitis B and C viruses, herpes viruses), veterinary disease agent (foot and mouth disease virus, prions, blue tongue virus), or plant virus (tobacco and cucumber viruses). The agent can also be an environmental toxin, such as herbicides, or superoxide anion in clinical samples.

In some embodiments, the agent is an agent of interest including known and unknown compounds that encompass numerous chemical classes, primarily organic molecules, which may include organometallic molecules, inorganic molecules, genetic sequences, etc.

Evaluating candidate drugs, including toxicity testing and the like can also be performed. Candidate agents also include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Also included as agents are pharmacologically active drugs, genetically active molecules, etc. Suitable compounds include, for example, chemotherapeutic agents, hormones or hormone antagonists, growth factors or recombinant growth factors and fragments and variants thereof. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

The agents include all of the classes of molecules described above, and may further comprise samples of unknown content, for instance, complex mixtures of naturally occurring compounds derived from natural sources such as plants. While many samples will comprise compounds in solution, solid samples that can be dissolved in a suitable solvent may also be assayed. Suitable samples include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Suitable samples include compounds being assessed for potential therapeutic value, i.e. drug candidates.

Agents such as chemical compounds, including candidate agents or candidate drugs, can be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In one embodiment, agents are screened for effect on a cell or tissue embedded in a silk-based transistor. A change in a parameter (e.g. a change in a parameter to indicate a change in the electrophysiological functionality) of the cell or tissue in response to the agent is measured, and the result is evaluated by comparison to a reference sample. A reference sample can be, for example, a cell or tissue in the absence of the same agent, or a cell or tissue in the presence of a positive control agent, where the agent is known to have an increase or decrease on at least one parameter of the electrophysiological functionality of the cell or tissue. In alternative embodiments, a reference sample is a negative control, i.e. where the cell or tissue is not exposed to an agent (i.e. there is an absence of an agent), or is exposed to an agent which is known not to give an effect on at least one parameter of the electrophysiological functionality of the cell or tissue.

In some embodiments, the agents may be in the form of a solution or a readily soluble form. In some embodiments, agent formulations contain a biologically active agent and a physiologically acceptable carrier, e.g. water, ethanol, DMSO, etc. Additional components, such as preservatives, may also be included in the agent formulation. However, if an agent is a liquid without a solvent, the formulation may contain the compound itself.

A plurality of assays comprising a silk-based transistor comprising cells or issues can be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype or electrophysiological functionality of a cell or tissue.

Optionally, a silk-based transistor comprising cells or issues used in a screen as disclosed herein can comprise cells which have been manipulated to express a desired gene product. Gene therapy can be used to either modify a cell to replace a gene product or add a heterologous gene product, or alternatively knock down a gene product endogenous to the cell.

In some embodiments the genetic engineering of a cell is done to treat disease. Techniques for genetically altering and transfecting cells are known by one of ordinary skill in the art. A skilled artisan could envision a multitude of genes which would convey beneficial properties to a cell. The desired gene for use in modification of a cell for use in silk-based transistor as disclosed herein can be transfected into the cell using a variety of techniques. For example, the gene is transfected into the cell using an expression vector. Suitable expression vectors include plasmid vectors (such as those available from Stratagene, Madison Wis.), viral vectors (such as replication defective retroviral vectors, herpes virus, adenovirus, adenovirus associated virus, and lentivirus), and non-viral vectors (such as liposomes or receptor ligands). A desired gene is usually operably linked to its own promoter or to a foreign promoter which, in either case, mediates transcription of the gene product. Promoters are chosen based on their ability to drive expression in restricted or in general tissue types, for example in mesenchymal cells, or on the level of expression they promote, or how they respond to added chemicals, drugs or hormones. Other genetic regulatory sequences that alter expression of a gene may be co-transfected. In some embodiments, the host cell DNA may provide the promoter and/or additional regulatory sequences. Other elements that can enhance expression can also be included such as an enhancer or a system that results in high levels of expression.

Methods of targeting genes in mammalian cells are well known to those of skill in the art (U.S. Pat. Nos. 5,830,698; 5,789,215; 5,721,367 and 5,612,205). By "targeting genes" it is meant that the entire or a portion of a gene residing in the chromosome of a cell is replaced by a heterologous nucleotide fragment. The fragment may contain primarily the targeted gene sequence with specific mutations to the gene or may contain a second gene. The second gene may be operably linked to a promoter or may be dependent for transcription on a promoter contained within the genome of the cell. In a preferred embodiment, the second gene confers resistance to a compound that is toxic to cells lacking the gene. Such genes are typically referred to as antibiotic-resistance genes. Cells containing the gene may then be selected for by culturing the cells in the presence of the toxic compound.

Methods of gene targeting in mammals are commonly used in transgenic "knockout" mice (U.S. Pat. Nos. 5,616,491; 5,614,396). These techniques take advantage of the ability of mouse embryonic stem cells to promote homologous recombination, an event that is rare in differentiated mammalian cells. Recent advances in human embryonic stem cell culture may provide a needed component to applying the technology to human systems (Thomson, 1998). Furthermore, the methods of the invention can be used to isolate and enrich for stem cells or progenitor cells that are capable of homologous recombination and, therefore, subject to gene targeting technology. Indeed, the ability to isolate and grow somatic stem cells and progenitor cells has been viewed as impeding progress in human gene targeting (Yanez & Porter, 1998).

The invention will be further characterized by the following examples which are intended to be exemplary of the embodiments.

The present invention can be defined in any of the following numbered paragraphs:

A silk-based light-emitting transistor comprising:
a substrate including a gate contact;
a silk dielectric layer positioned over the substrate;
at least one active layer comprising an organic semiconducting light-emitting material positioned over the silk dielectric layer; and
source and drain contacts positioned over the active layer.

The silk-based light-emitting transistor of paragraph 123, wherein the source, drain and gate contacts, substrate, active layer and silk dielectric layer are biocompatible.

The silk-based light-emitting transistor of paragraph 123, wherein the source, drain, or gate contact is a metal or metal oxide selected from the group consisting of gold, copper, iron, aluminum, indium-tin-oxide, and combination thereof.

The silk-based light-emitting transistor of paragraph 123, wherein the active layer is p-type, n-type or p-n junction type.

The silk-based light-emitting transistor of paragraph 123, wherein the active layer is a combination of multiple layers which present charge transport and/or light emitting properties.

The silk-based light-emitting transistor of paragraph 123, wherein the organic semiconducting light-emitting material is a thiophene derivative, a perylene derivative, a fluorine derivative, or a phenyl derivative.

The silk-based light-emitting transistor of paragraph 123, wherein the active layer further comprises one or more light-emitting elements.

The silk-based light-emitting transistor of paragraph 129, wherein the light-emitting element is selected from the group consisting of organometallic complexes, organic dyes, semiconducting quantum dots, metal nanoparticles and combinations thereof.

The silk-based light-emitting transistor of paragraph 123, wherein the substrate, gate contact, and dielectric layer are transparent.

The silk-based light-emitting transistor of paragraph 123, wherein the source and drain contacts are transparent.

An implantable device comprising the silk-based light-emitting transistor of any one of paragraphs 123-132.

A sensing device comprising the silk-based light-emitting transistor of any one of paragraphs 123-132.

A silk-based transistor comprising:
a substrate including a gate contact;
a silk dielectric layer positioned over the substrate;
at least one active layer comprising a silk matrix doped with an organic semiconducting material positioned over the silk dielectric layer; and
source and drain contacts positioned over the active layer.

The silk-based transistor of paragraph 135, wherein the source, drain and gate contacts, substrate, active layer and silk dielectric layer are biocompatible.

The silk-based transistor of paragraph 135, wherein the silk dielectric layer further comprises one or more non-conducting biocompatible polymers.

The silk-based transistor of paragraph 135, wherein the source, drain, or gate contact is a metal or metal oxide selected from the group consisting of gold, copper, iron, aluminum, indium-tin-oxide, and combination thereof.

The silk-based transistor of paragraph 135, wherein the active layer is p-type, n-type or p-n junction.

The silk-based transistor of paragraph 139, wherein the active layer is a combination of multiple layers which present charge transport and/or light emitting properties.

The silk-based transistor of paragraph 135, wherein the organic semiconducting material presents light-emitting property.

The silk-based transistor of paragraph 135, wherein the organic semiconducting material is a thiophene derivative, a perylene derivative, a fluorine derivative, or a phenyl derivative.

The silk-based transistor of paragraph 135, wherein the active layer further comprises one or more light-emitting elements.

The silk-based transistor of paragraph 143, wherein the light emitting element is selected from the group consisting of organometallic complexes, organic dyes, semiconducting quantum dots, metal nanoparticles and combinations thereof.

The silk-based transistor of paragraph 135, wherein the silk-based transistor is a biocompatible field-effect transistor.

The silk-based transistor of paragraph 135, wherein the silk-based transistor is a biocompatible light-emitting transistor.

The silk-based transistor of paragraph 146, wherein the substrate, gate contact, and dielectric layer are transparent.

The silk-based transistor of paragraph 147, wherein the source and drain contacts are transparent.

A silk-based transistor comprising:
a substrate including a gate contact;
a dielectric layer positioned over the substrate;
at least one active layer comprising a silk matrix embedded with an electronically active biological material positioned over the dielectric layer; and
source and drain contacts in contact with the active layer.

The silk-based transistor of paragraph 149, wherein the source, drain and gate contacts, substrate, active layer and dielectric layer are biocompatible.

The silk-based transistor of paragraph 149, wherein the dielectric layer is silk matrix.

The silk-based transistor of paragraph 151, wherein the silk dielectric layer further comprises one or more non-conducting biocompatible polymers.

The silk-based transistor of paragraph 149, wherein the source, drain, or gate contact is a metal or metal oxide selected from the group consisting of gold, copper, iron, aluminum, indium-tin-oxide, and combination thereof.

The silk-based transistor of paragraph 149, wherein the electronically active biological material is an excitable cell, tissue or organism.

The silk-based transistor of paragraph 149, wherein the cell, tissue or organism comprises ion channels.

An implantable device comprising the silk-based transistor of any one of paragraphs 135-155.

A sensing device comprising the silk-based transistor of any one of paragraphs 135-155.

A method of evaluating an activity of an electronically active biological material, comprising:
providing a silk-based electronic device comprising:
a substrate including a gate contact;
a dielectric layer positioned over the substrate;
at least one active layer comprising a silk matrix embedded with the electronically active biological material positioned over the dielectric layer; and
source and drain contacts in contact with the active layer;
exposing the electronically active biological material to a stimulant to produce or change a parameter of the silk-based electronic device; and
evaluating the activity of the biological material based on the parameter or change of the parameter of the silk-based electronic device.

The method of paragraph 158, wherein the electronically active biological material is an excitable cell, tissue or organism.

The method of paragraph 158, wherein the cell, tissue or organism comprises ion channels.

The method of paragraph 158, wherein the parameter of the silk-based electronic device is an electrical signal.

The method of paragraph 158, further comprising exposing the electronically active biological material to an optical device, and monitoring the activity of the biological material with parameters of the optical device.

A method of identifying an agent that modulates an activity of an electronically active biological material, comprising:
providing a silk-based electronic device comprising:
a substrate including a gate contact;
a dielectric layer positioned over the substrate;
at least one active layer comprising a silk matrix embedded with the electronically active biological material positioned over the dielectric layer; and
source and drain contacts in contact with the active layer;
measuring a first parameter of the silk-based electronic device;
exposing the electronically active biological material to an agent;
measuring a second parameter of the silk-based electronic device; and comparing the second and first parameters of the silk-based electronic device before and after the exposing step, wherein a change in parameters indicates the agent is capable of modulating the activity of the biological material.

The method of paragraph 163, wherein the electronically active biological material is an excitable cell, tissue or organism.

The method of paragraph 164, wherein the cell, tissue or organism comprises ion channels.

The method of paragraph 163, wherein the first and second parameters of the silk-based electronic device are electrical signals.

The method of paragraph 163, further comprising monitoring the optical parameters of the biological material before and after the exposing step with an optical device.

The invention is not limited to the particular methodology, protocols, and reagents, etc., described herein and as such may vary. The terminology used herein is for the purpose of describing particular embodiments only, and is not intended to limit the scope of the invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

Silk-Based n-Type Field Effect Transistor

Figure 2:
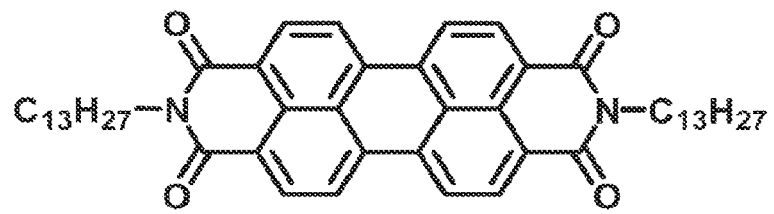
FIG. 2 shows the molecular structure of the N,N'-ditridecylperylene-3,4,9,10-tetracarboxylic diimide (P13)

FIG. 1 shows a top configuration of typical field effect transistor architecture. Silk fibroin solution (7% w/v) was used to spin coat a crosslinked silk dielectric film (~600 nm) onto a glass/patterned indium-tin-oxide (ITO) (transparent substrate/gate) substrate, with a patterned ITO acting as a gate contact. On top of the silk film, a prototypical n-type semiconducting compound for electron conduction, namely the N,N'-ditridecylperylene-3,4,9,10-tetracarboxylic diimide (P13) (molecular structure shown in FIG. 2), was vacuum-deposited at a sublimation rate of 0.1 Å/s until a thickness of 15 nm was reached. A 50 nm-thick source and drain gold contacts were vacuum thermo-deposited through a metal mask completing a typical top-contact organic field-effect transistor (OFET) configuration.

The silk-based transistor can be operated and characterized by a probe station equipped with a parametric analyzer both in atmosphere controlled dry-box systems and in air-room temperature. The standard output and transfer curves are illustrated in FIG. 3 and FIG. 4.

Figure 3:
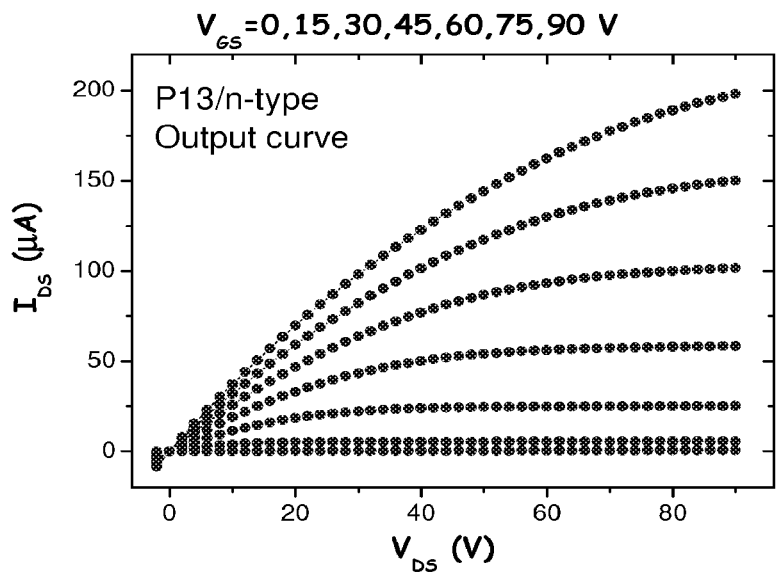
FIG. 3 is a graph showing the output curve of the fabricated silk-based n-type transistor.

The measured output curves in FIG. 3 show performance of the silk-based transistor, with a linear behavior at the initial drain-source (d-s) voltages and then saturation together with a common origin.

Figure 4:
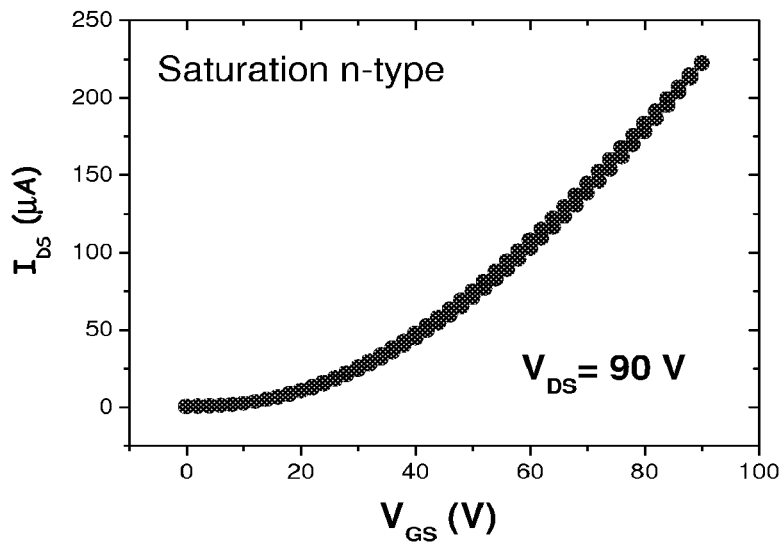
FIG. 4 is a graph showing the saturation curve of the fabricated silk-based n-type transistor.

The excellent electrical behavior of the silk-based transistor is confirmed by the saturation curves shown in FIG. 4. Saturation curves were measured at $V_{d-s}=\pm 90V$, where $V_{d-s}$ represents the voltage between drain-source contacts depending on the n- or p-type semiconducting material. Going from 0 to 90V of the scanning gate-source potential and backward from 90V to 0V for the fixed drain-source voltage of 90V, there were almost no hysteresis processes (the two curves almost coincide). This is an indication of very low or absent charge trapping of the silk dielectric layer.

The parameters describing the performance of the n-type silk-based transistor, namely charge mobility $\mu_n$ (in the case of an n-type semiconductor, such as P-13, the major mobile charge are electrons) and voltage threshold, $V_{th}$, may be derived from the curves. In this case, for the silk-P13 transistor described above, charge mobility $\mu_n=0.2$ cm$^2$/Vs and voltage threshold $V_{th}=1.6$ V. Note that the values charge mobility are in accordance with the charge mobility of standard SiO$_2$ gated OFETs; the measured voltage threshold of silk-P13 transistor are better as compared to values for standard silicon based P13 transistors (See, e.g., Dinelli et al., 18 Adv. Mater. 1416-20 (2006); Gundlach et al., 98 J. Appl. Phys. 4502-09 (2005); Malenfant et al., 14 Appl. Phys. Lett. 2517-19 (2002); Chesterfield et al., 108 J. Phys. Chem. B 19281-292 (2004)). Silk can therefore be used to replace conventional SiO$_2$ or plastic (typically PMMA) dielectric layers, slowing high field effect mobility in organic thin film transistors.

Example 2

Silk-Based p-Type Field Effect Transistor

Figure 5:
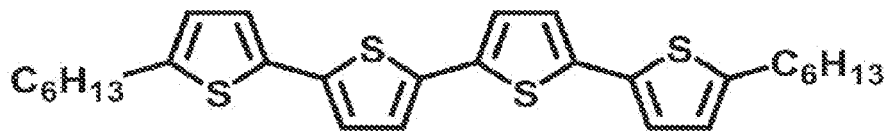
FIG. 5 shows the molecular structure of α,ω-dihexyl-quaterthiophene (DH4T).
Figure 6:
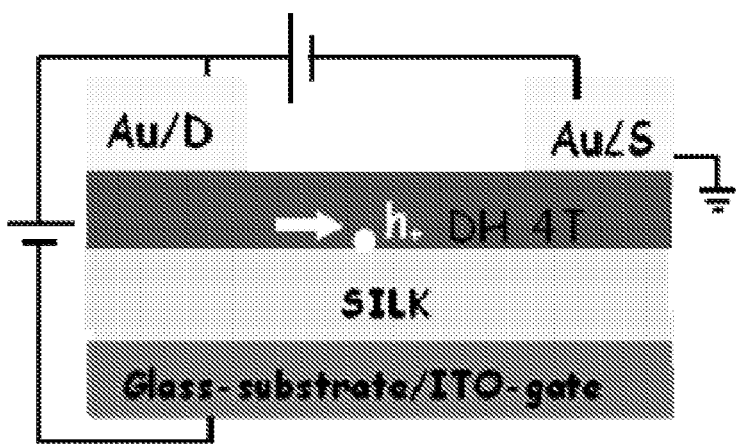
FIG. 6 is a schematic depicting a silk-based p-type transistor in top contact configuration.

Similarly to the manner the silk-based n-type transistor was fabricated, a p-type silk-based transistor in the top contact configuration was fabricated as shown in FIG. 6. Silk fibroin solution (7% w/v) was used to spin coat a crosslinked silk dielectric film (~600 nm) onto a glass/patterned indium-tin-oxide (ITO) (transparent substrate/gate) substrate, with a patterned ITO acting as a gate contact. On top of the silk film, a prototypical p-type semiconducting compound, namely the α,ω-dihexyl-quaterthiophene (DH4T) (molecular structure as shown in FIG. 5), was vacuum-deposited at a sublimation rate of 0.1 Å/s until a thickness of 15 nm was reached. A 50 nm-thick source and drain gold contacts were vacuum thermo-deposited through a metal mask completing a typical top-contact organic field-effect transistor (OFET) configuration.

Figure 7:
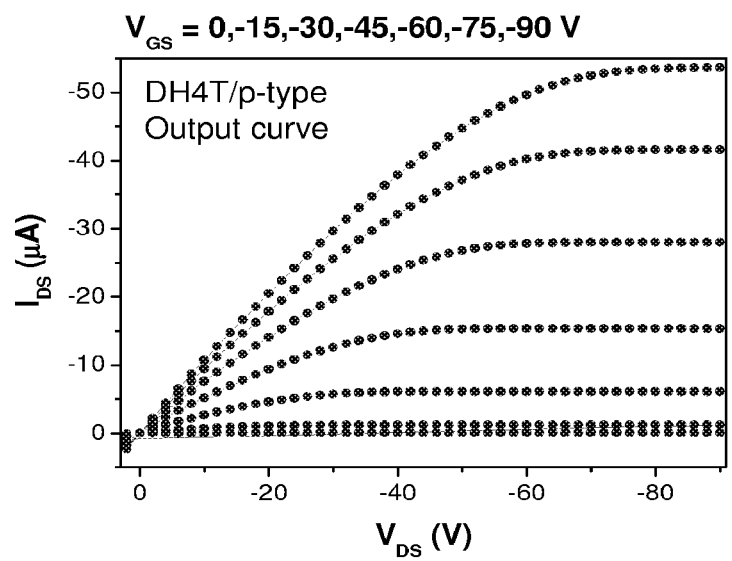
FIG. 7 is a graph showing the output curve of the fabricated silk-based p-type transistor.

Following similar methodology described above for silk-based n-type transistor, the silk-based p-type transistor was operated and characterized by a probe station equipped with a parametric analyzer both in atmosphere controlled dry-box systems and in air-room temperature. The standard output and saturation curves are shown in FIG. 7 and FIG. 8.

Similarly as the silk-based n-type transistors, the excellent performance may be demonstrated for the silk-based p-type transistors. From the output curves of FIG. 7, the parameters describing the performances of the p-type silk-based transistor, namely charge mobility $\mu_p$ (in the case of an p-type semiconductor, such as DH4T, the major mobile charge are holes) and voltage threshold, $V_{th}$, may be derived from the curves. In this case, for the silk-DH4T p-type transistor described above, charge mobility $\mu_p=1.3\times10^{-2}$ cm$^2$/Vs and voltage threshold $V_{th}=18$ V. Again, the determined values are superior to what has been reported for standard silicon-based DH4T transistors (See, e.g., Dinelli et al., 2006).

Figure 8:
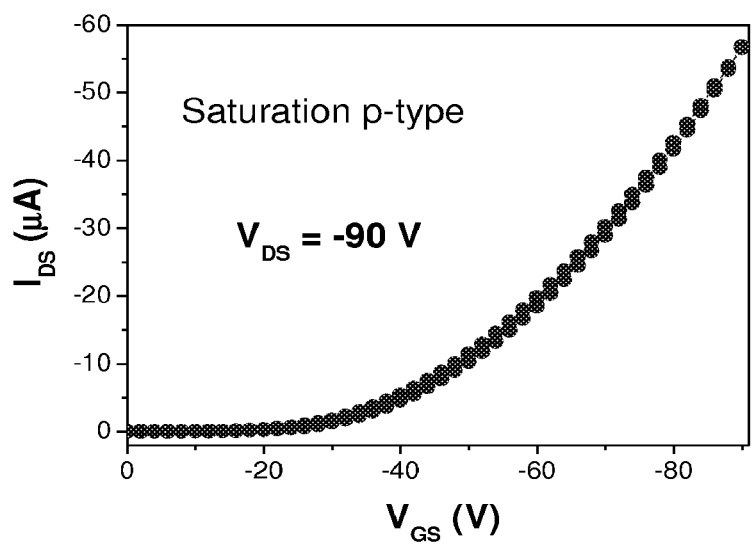
FIG. 8 is a graph showing the saturation curve of the fabricated silk-based p-type transistor.

The saturation curves of silk-DH4T transistor measured at $V_{d-s}=\pm90$ V are illustrated in FIG. 8. The two almost overlapping lines are for forward and backward scanning of the gate-source voltage while keeping constant the $V_{d-s}$. These data indicate almost no-hysteresis and consequent low charge trapping of the silk dielectric layer in particular for electron transport (i.e., the silk-P13 device). Therefore, silk can be used to replace conventional SiO$_2$ or plastic dielectric layers, allowing high field effect mobility in organic thin film transistors.

Example 3

Silk-Living Cell Electronic Device

A silk-gel may be obtained via the physical crosslinking of the hydrophobic domains in the silk, resulting in beta sheet crosslinks. These interactions stabilize the silk, resulting in insolubility in aqueous systems.

Figure 11:
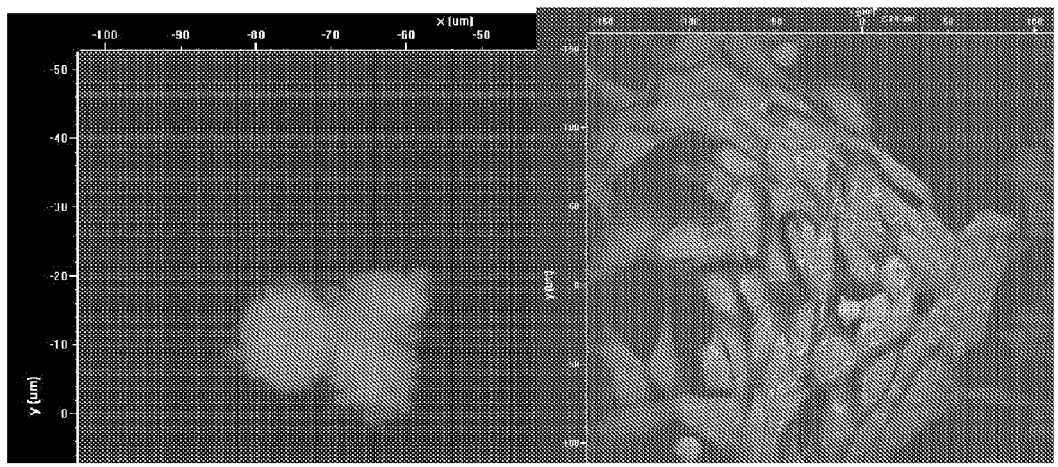
FIG. 11 shows the confocal images of silk-gel infiltrated with physiological saline solution and astroglial cells.

A preparation of astroglial primary cells may be added with a standard physiological saline buffer solution. The cells entered the silk-gel matrix maintaining viability over 2 months under ambient conditions. The demonstration of bioactive features of the silk-gel system with primary astroglial cells was confirmed by confocal microscopy as shown in FIG. 11.

Figure 12A:
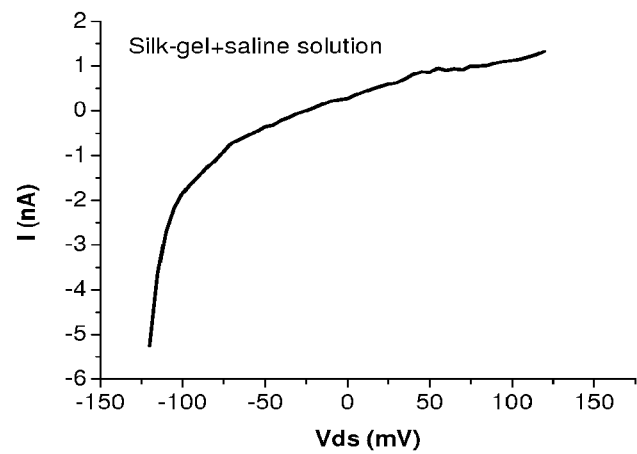
FIGS. 12A and 12B show the output curves of silk-cells device (12B, silk-gel infiltrated with saline solution and astroglial cells) compared to the control (12A, silk-gel infiltrated with saline solution, without cells).
Figure 12B:
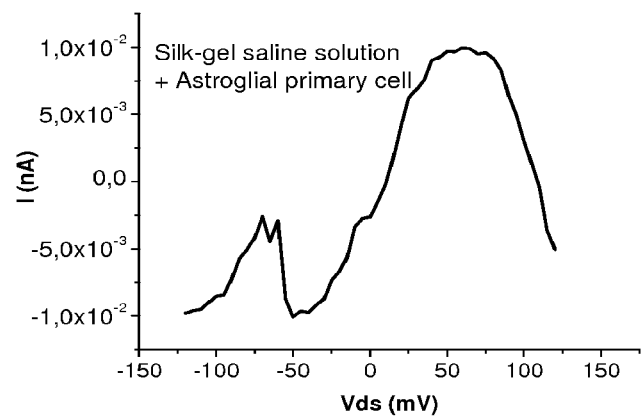

The silk-gel systems infiltrated with physiological saline solution and the astroglial cells were moved to the top of the device. For comparison, blank control samples were prepared following the same protocol of fabrication and manipulation, with the silk-gel and the physiological saline solution in absence of the cells. Operating the device with a drain-source voltage ($V_{d-s}$) ranging from −150 mV to 120 mV, the control sample showed a typical, reproducible and stable behavior of the Id-s current measured for each $V_{d-s}$ step after a delay time of 300 msec, as shown in FIGS. 12A and 12B.

The device containing the living astroglial cells measures an $I_{d-s}$ current in the pico-ampere range compared to the nano-ampere range of the control sample containing silk-gel and saline buffer solution without the cells. Moving from a $V_{d-s}$ value of −120 mV up to +120 mV, the behavior of $I_{d-s}$ shows a trough at −50 mV and a peak at +70 mV (FIG. 12B) with a behavior very different from the control sample. The experiment can be reproduced several times at ambient conditions.

Figure 13:
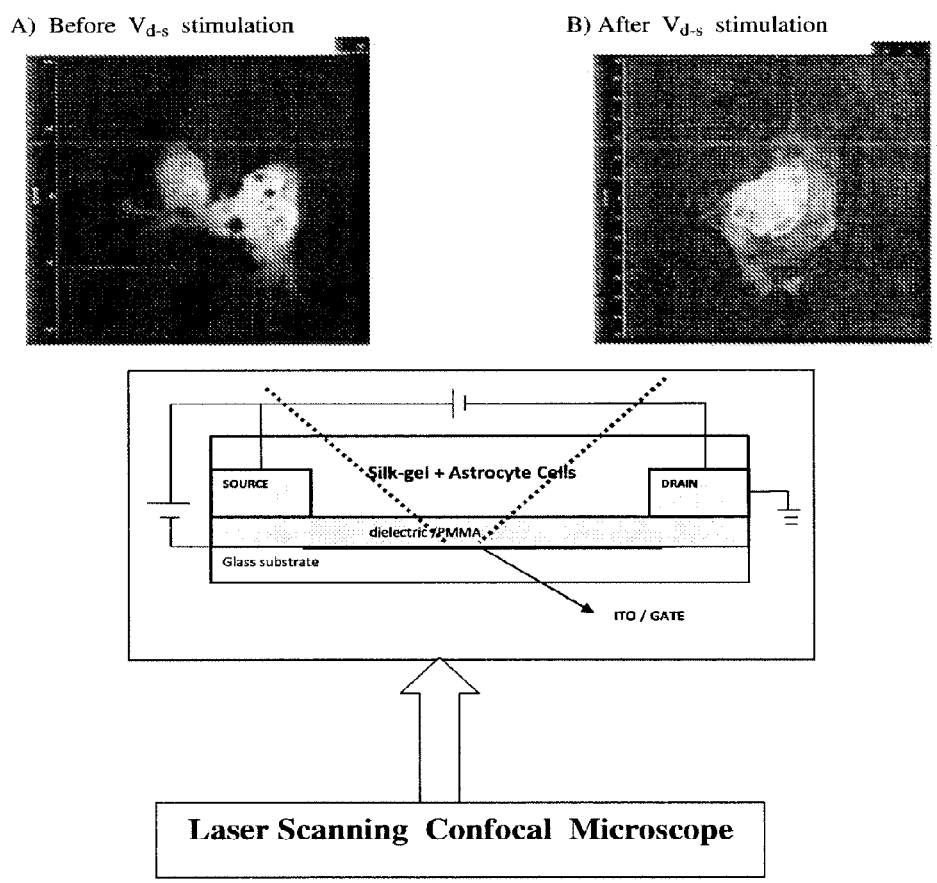
FIGS. 13A and 13B show the results of simultaneous measurements of Laser Scanning Confocal Microscope (LSCM) imaging of astroglial cells in the silk-cells device before (13A) and after (13B) Vd-s cycling.

Additionally, other physical behavior can be integrated into the silk-biological material based electronic device, since silk fibroin can be used to host a multifunctional material system. For example, optical and electronic properties (with living primary cells) can be combined and integrated into the devices (i.e., the transistors). In FIG. 13, Laser Scanning Confocal images of the silk-based device with the astroglial cells are shown during operation. After the $V_{d-s}$ cycling, a stimulation for cells, the astroglial cellular volume changed. This is in agreement with conventional electrophysiology due to ion-channels cellular membrane activity.

Example 4

Silk-Based Light-Emitting Transistor

Figure 14:
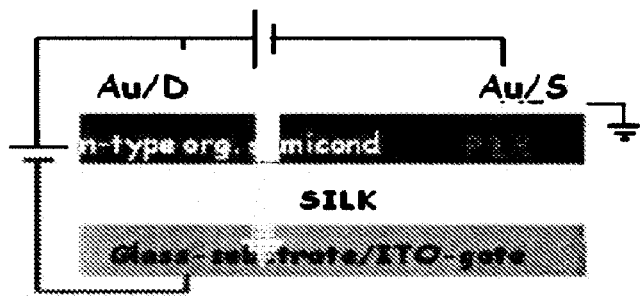
FIG. 14 is a schematic showing the silk-based unipolar (n-type) light-emitting transistor in top contact configuration.
Figure 15:
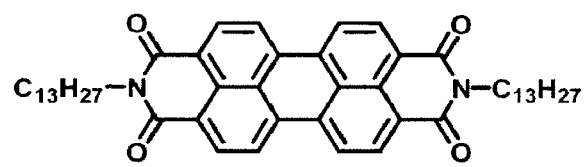
FIG. 15 shows the molecular structure of the N,N'-ditridecylperylene-3,4,9,10-tetracarboxylic diimide (P13).

A typical field effect transistor architecture using the top configuration, shown in FIG. 14, was used as a starting point for building a light-emitting transistor. Silk fibroin solution (7% w/v) was used to spin coat a crosslinked silk film onto a glass/patterned ITO (transparent substrate/gate) substrate. On top of the silk film, a prototypical semiconducting compound of n-type unipolar light-emitting material, namely the N,N'-ditridecylperylene-3,4,9,10-tetracarboxylic diimide (P13) (molecular structure shown in FIG. 15) was vacuum deposited at a sublimation rate of 0.1 Å/s until a thickness of 15 nm is reached. A 50 nm thick source and drain gold contacts are vacuum thermo-deposited through a metal mask completing a typical top-contact configuration.

The silk-based light-emitting unipolar n-type transistor can be operated and characterized by a probe station equipped with a parametric analyzer both in atmosphere controlled dry-box systems and in air-room temperature.

Figure 16:
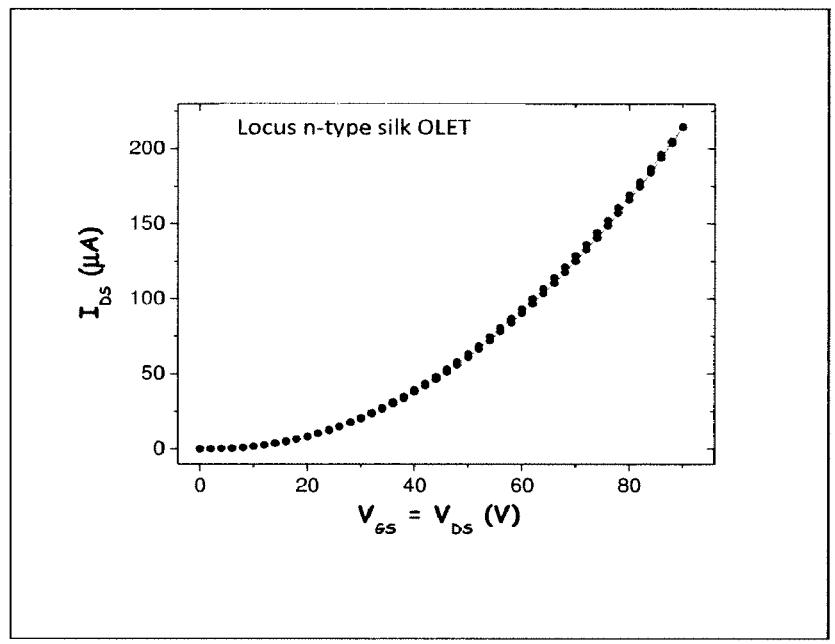
FIG. 16 is a graph showing the locus curves of the n-type unipolar silk-based light emitting transistor.

Locus curve, namely the drain-source current toward the scanning of gate-source and drain-source at the same potential voltage, for the properties of light-emitting transistor was plotted. The locus curve of the fabricated unipolar n-type silk-based light-emitting transistor is shown in FIG. 16.

Scanning the $V_{gs}=V_{ds}$ from 0V to 90V and backward from 90V to 0V, the investigated device showed almost no hysteresis. This result indicates that no leaking current and almost no trapping of electron charge carriers in the silk dielectric layer.

Figure 17:
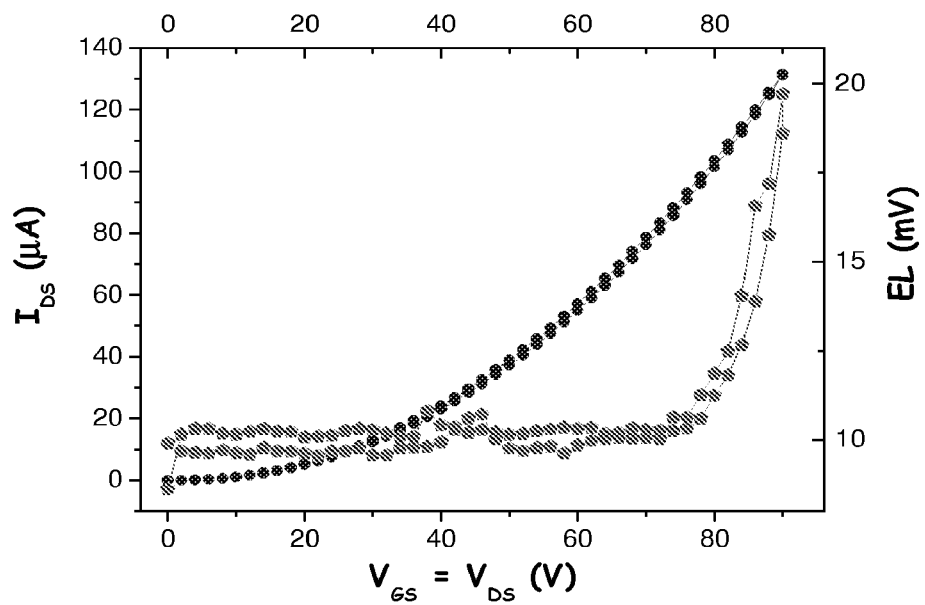
FIG. 17 is a graph showing the locus curves (circles) and the detected light-emission (pentagons) from the unipolar n-type (P13) silk-based light-emitting transistor.

The operated (in locus mode) silk-based light-emitting device was coupled to a light detector, such as a photodiode or a photomultiplier, for example, for light-emission measurements. The results are shown in FIG. 17.

A nonlinear intensity of emitted light started at a $V_{gs}=V_{ds}$ of 75V. The performance of the fabricated device is favorable compared to unipolar silicon-based organic light-emitting transistors previously reported. The sensitive parameters assessing the performance of the device were: $V_{th}=1.4$ V; $\mu_n=0.13$ cm$^2$/Vs; and the estimated light emission intensity was equal to or better than 2000 Cd/m$^2$.

What is claimed is:

1. A silk-based transistor comprising:
    a substrate including a gate contact;
    a silk dielectric layer positioned over the substrate;
    at least one active layer positioned over the silk dielectric layer comprising:
        an organic semiconducting material; and
        a silk matrix embedded with an electronically active biological material
        comprising excitable living cells, tissues, and/or organisms; and
    source and drain contacts positioned over the active layer,
    wherein the silk-based transistor is characterized in that activity and/or functionality of the excitable living cells, tissues, and/or organisms is modulated when exposed to an agent and/or an electric field.

2. The silk-based transistor of claim 1, wherein the source, drain and gate contacts, substrate, active layer and silk dielectric layer are biocompatible.

3. The silk-based transistor of claim 1, wherein the source, drain, or gate contact is a metal or metal oxide selected from the group consisting of gold, copper, iron, aluminum, indium-tin-oxide, and combination thereof.

4. The silk-based transistor of claim 1, wherein the organic semiconducting material is p-type, n-type or p-n junction type.

5. The silk-based transistor of claim 1, wherein the active layer is a combination of multiple layers which present charge transport and/or light emitting properties.

6. The silk-based transistor of claim 1, wherein the organic semiconducting material is selected from a group consisting of: thiophene derivatives, perylene derivatives, fluorine derivatives, phenyl derivatives, organometallic complexes, organic dyes, semiconducting quantum dots, metal nanoparticles and any combinations thereof.

7. The silk-based transistor of any one of claims 1-6, wherein the organic semiconducting material is light-emitting.

8. The silk-based transistor of claim 1, wherein the active layer further comprises one or more light-emitting elements.

9. The silk-based transistor of claim 8, wherein the light emitting element is selected from the group consisting of organometallic complexes, organic dyes, semiconducting quantum dots, metal nanoparticles and combinations thereof.

10. The silk-based transistor of any of claims 1-6, wherein the silk dielectric layer further comprises one or more non-conducting biocompatible polymers.

11. The silk-based transistor of any of claims 1-6, wherein the excitable living cells, tissues, and/or organisms comprises ion channels.

\* \* \* \* \*